US008865679B2

(12) United States Patent
Ostroff

(10) Patent No.: US 8,865,679 B2
(45) Date of Patent: *Oct. 21, 2014

(54) USE OF BETA-GLUCANS AGAINST BIOLOGICAL WARFARE WEAPONS AND PATHOGENS INCLUDING ANTHRAX

(75) Inventor: Gary R. Ostroff, Worcester, MA (US)

(73) Assignee: Biothera, Inc., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/871,541

(22) Filed: Aug. 30, 2010

(65) Prior Publication Data

US 2011/0033475 A1  Feb. 10, 2011

Related U.S. Application Data

(63) Continuation of application No. 10/268,201, filed on Oct. 9, 2002, now Pat. No. 7,786,094.

(60) Provisional application No. 60/328,206, filed on Oct. 9, 2001.

(51) Int. Cl.
| | | |
|---|---|---|
| A61K 31/716 | (2006.01) | |
| C08B 37/00 | (2006.01) | |
| A61K 31/715 | (2006.01) | |
| A61K 39/395 | (2006.01) | |
| A61K 45/06 | (2006.01) | |

(52) U.S. Cl.
CPC .............. *A61K 31/715* (2013.01); *A61K 31/716* (2013.01); *C08B 37/0024* (2013.01); *A61K 39/395* (2013.01); *A61K 45/06* (2013.01)
USPC ........................................ 514/54; 536/123.12

(58) Field of Classification Search
None
See application file for complete search history.

(56) References Cited

U.S. PATENT DOCUMENTS

| | | | | |
|---|---|---|---|---|
| 4,739,046 | A | 4/1988 | Di Luzio | |
| 4,810,646 | A | 3/1989 | Jamas et al. | |
| 4,992,540 | A | 2/1991 | Jamas et al. | |
| 5,028,703 | A | 7/1991 | Jamas et al. | |
| 5,032,401 | A | 7/1991 | Jamas et al. | |
| 5,037,972 | A | 8/1991 | Jamas et al. | |
| 5,057,503 | A | 10/1991 | Czop et al. | |
| 5,082,936 | A | 1/1992 | Jamas et al. | |
| 5,223,491 | A | 6/1993 | Donzis | |
| 5,250,436 | A | 10/1993 | Jamas et al. | |
| 5,322,841 | A | 6/1994 | Jamas et al. | |
| 5,397,773 | A | 3/1995 | Donzis | |
| 5,488,040 | A * | 1/1996 | Jamas et al. ..................... | 514/54 |
| 5,504,079 | A * | 4/1996 | Jamas et al. ..................... | 514/54 |
| 5,506,124 | A | 4/1996 | Jamas et al. | |
| 5,532,223 | A | 7/1996 | Jamas et al. | |
| 5,576,015 | A | 11/1996 | Donzis | |
| 5,622,940 | A * | 4/1997 | Ostroff ............................ | 514/54 |
| 5,633,369 | A | 5/1997 | Jamas et al. | |
| 5,663,324 | A | 9/1997 | James et al. | |
| 5,702,719 | A | 12/1997 | Donzis | |
| 5,705,184 | A | 1/1998 | Donzis | |
| 5,741,495 | A * | 4/1998 | Jamas et al. ................. | 424/278.1 |
| 5,783,569 | A * | 7/1998 | Jamas et al. ..................... | 514/54 |
| 5,811,542 | A | 9/1998 | Jamas et al. | |
| 5,817,643 | A | 10/1998 | Jamas et al. | |
| 5,849,720 | A | 12/1998 | Jamas et al. | |
| 6,020,324 | A | 2/2000 | Jamas et al. | |
| 6,143,731 | A | 11/2000 | Jamas et al. | |
| 6,355,625 | B1 * | 3/2002 | Pavliak et al. ................... | 514/54 |
| 6,355,642 | B1 | 3/2002 | Koyama et al. | |
| 6,369,216 | B1 * | 4/2002 | Patchen et al. ........... | 536/123.12 |
| 6,387,665 | B1 | 5/2002 | Ivins et al. | |
| 6,413,715 | B2 | 7/2002 | Wakshull et al. | |
| 6,573,245 | B1 | 6/2003 | Marciani | |
| 7,022,685 | B2 | 4/2006 | Patchen et al. | |
| 7,786,094 | B2 * | 8/2010 | Ostroff ............................ | 514/54 |
| 2009/0226528 | A1 * | 9/2009 | Czech et al. ................... | 424/491 |

OTHER PUBLICATIONS

Merriam-Webster's Collegiate Dictionary, Tenth Edition, published 1998 by Merriam-Webster, Incorporated, p. 924.*
The Merck Manual of Diagnosis and Therapy, Seventeenth Edition, published 1999 by Merck Research Laboratories, pp. 1157-1158.*
Vetvicka et al., "Pilot Study: Orally-Administered Yeast beta 1,3-glucan Prophylactically Protects Against Anthrax Infection and Cancer in Mice" JANA (2002) vol. 5 No. 1, pp. 1-5.*
U.S. Appl. No. 10/268,201, filed Oct. 9, 2002, Olson et al.
Babineau et al., "A Phase II Multicenter, Double-blind, Randomized, Placebo-Controlled Study of Three Dosages of an Immunomodulator (PGG-Glucan) in High-Risk Surgical Patients," *Archives of Surgery*, 1994; 129(11):1204-1210.
Ballard et al., "Anthrax toxin-mediated delivery of a cytotoxic T-cell epitope in vivo," *PNAS*, Oct. 1996; 93:12531-12534.
Bernabeu et al., "Procedure to Evaluate the Stability during Processing and Storage of a Medicated Premix and Medicated Farm Feed: Erythromycin Thiocyanate," *Journal of Agricultural and Food Chemistry*, 2001; 49(8):3709-3712.
Blaylock, "Yeast β1,3-glucan and Its Use Against Anthrax Infection and in the Treatment of Cancer," *JANA*, 2002 Spring; 5(1):3-4. Editorial Commentary.

(Continued)

*Primary Examiner* — Eric Olson
(74) *Attorney, Agent, or Firm* — Mueting, Raasch & Gebhardt, P.A.

(57) ABSTRACT

The present invention provides a means to broadly protect the military and the public from injury from biological warfare weapons, particularly infective agents such as anthrax. Beta (1,3)-glucans, particularly whole glucan particles, PGG-Glucan, and microparticulate glucan, provide general immune enhancement, thereby increasing the body's ability to defend against a wide variety of biological threats. Beta (1,3)-glucans have been shown to increase the resistance to infection by anthrax and other infectious organisms when administered before and after infection. The anti-infective mechanism of β(1,3)-glucan appears to involve stimulation of the innate immune system through increased cytokine release and CR3 receptor activation. Beta (1,3)-glucan is pharmaceutically stable, relatively compact, and can also be used without significant side effects. Beta (1,3)-glucan can also enhance the effectiveness of other medical countermeasures such as antibiotics, vaccines, and immune antibodies.

12 Claims, 9 Drawing Sheets

(56) References Cited

OTHER PUBLICATIONS

Bowers et al., "Glucan Enhances Survival in an Intraabdominal Infection Model," *J. Surg. Res.*, Aug. 1989; 47(2):183-8.
Brossier et al., "Role of Toxin Functional Domains in Anthrax Pathogenesis," *Infection and Immunity*, Apr. 2000; 68(4):1781-1786.
Browder et al., "Synergistic Effect of Nonspecific Immunostimulation and Antibiotics In Experimental Peritonitis," *Surgery*, 1987; 102(2):206-214.
Franz et al., "Clinical Recognition and Management of Patients Exposed to Biological Warfare Agents," *JAMA*, 1997; 278(5):399-411.
Fritz et al., "Pathology of experimental inhalational anthrax in the rhesus monkey," *Lab Invest.*, 1995; 73:691-702.
Hanna et al., "On the role of macrophages in anthrax," *PNAS*, 1993; 90:10198-10201.
Helland et al., "Protective Effect of Beta-Glucan Against *Myobacterium bovis*, BCG Infection in BALB/c Mice," *Scand. J. Immunol.*, Jun. 1998; 47(6):548-53.
Inglesby et al., "Anthrax as a Biological Weapon: Medical and Public Health Management," *JAMA*, 1999; 281(18):1735-45.
Kaiser et al., "Synergism between Poly-(1-6)-β-D-Glucopyranosyl-(1-3)-β-D-Glucopyranose Glucan and Cefazolin in Prophylaxis of Staphylococcal Wound Infection in a Guinea Pig Model," *Antimicrobial Agents and Chemotherapy*, 1998; 42(9):2449-2451.
Kemodle et al., "Prophylactic Anti-Infective Activity of Poly-[1-6]-β-D-Glucopyranosyl-[1-3]-β-D-Glucopyranose Glucan in a Guinea Pig Model of Staphylococcal Wound Infection," *Antimicrobial Agents and Chemotherapy*, 1998; 42(3):545-549.
Pellizzari et al., "Anthrax lethal factor cleaves MKK3 in macrophages and inhibits the LPS/IFNγ-induced release of NO and TNFα," *FEBS*, 1999; 462:199-204.
Solokhin et al., *Zhurnal Mikrobiologii Epi. Immuno.*, 1995; 5:72-76. English Abstract.
Tzianabos et al., "Protection Against Experimental Intraabdominal Sepsis by Two Polysaccharide Immunomodulators," *J. Infect. Dis.*, Jul. 1998;178(1):200-6.
U.S. Government Printing Office, Office of Technology Assessment, U.S. Congress, Washington, D.C., "Proliferation of Weapons of Mass Destruction," 1993; pp. 53-55.
Welkos et al., "Differences in Susceptibility of Inbred Mice to *Bacillus anthracis*," *Infection and Immunity*, Mar. 1986; 51(3):795-800.
World Health Organization, *Health Aspects of Chemical and Biological Weapons*, Geneva, Switzerland, 1970; pp. 98-99.
Almdahl et al., "The Effect of Splenectomy on *Escheria coli* Sepsis and its Treatment with Semisoluble Aminated Glucan," *Scand. J. Gastroenterol.*, Apr. 1987; 22(3):261-267.
Browder, W., "Role of Immunomodulation in Surgical Infections," *Serv. Immunol. Res.*, 1983; 2(3):299-301.
Browder et al., "Modification of Post-Operative *C. albicans* Sepsis by Glucan Immunostimulation," *Int. J. Immunopharmac.*, 1984; 6(1):19-26.
Browder et al., "Protective Effect of Nonspecific Immunostimulation in Postsplenectomy Sepsis," *J. Surg. Res.*, Dec. 1983; 35(6):474-479.
Browder et al., "Beneficial Effect of Enhanced Macrophage Function in the Trauma Patient," *Ann. Surg.*, 1990; 211(5):605-613.
Compton et al., "The Beneficial Effect of Enhanced Macrophage Function on the Healing of Bowel Anastomoses," *Am. Surg.*, Jan. 1996; 62(1); 9 pgs.
de Felippe, Jr. et al., "Infection Prevention in Patients with Severe Multiple Trauma with the Immunomodulator Beta 1-3 Polyglucose (Glucan)," *Surg. Gynecol. Obstet.*, Oct. 1993, 177(4):383-388.
Di Luzio, N. R., "Modification of Diverse Experimental Immunosuppressive States by Glucan," *Surv. Immunol. Res.*, Jul. 1985; 4(2):160-167.
Di Luzio, N. R., "Update on the Immunomodulating Activities of Glucans," *Springer Semin. Immunopathol,*, 1985; 8:387-400.
Glovsky et al., "Effects of Particulate β-1,3 Glucan on Human, Rat, and Guinea Pig Complement Activity," *J. Reticuloendothel. Soc.*, May 1983; 33(5):401-413.

Gordon et al., "A Placebo-Controlled Trial of the Immune Modulator, Lentinan, in HIV-Positive Patients: A Phase I/II Trial," *J. Med.*, 1998; 29(5 & 6):305-330.
Guidi-Rontoni et al., "Germination of *Bacillus anthracis* spores within alveolar macrophages," *Molecular Microbiology*, 1999; 31(1):9-17.
Hetland et al., "Protective Effect of β-Glucan Against Systemic *Streptococcus pneumoniae* Infection in Mice," *FEMS Immunol. Med. Microbiol.*, 2000; 27:111-116.
Hull et al., "The Interaction of Glucan and Cefoxitin in Prevention of Murine Abscess," *Curr. Surg.*, Sep./Oct. 1986; 43(5):416-418.
Kanai et al., "β-1, 3 Glucan as an Immunopotentiator Against Experimental Tuberculous Infection in Mice," (author's transl.), *Kekkaku*, 1980; 55(8):371-374. English abstract only.
Konopski et al., "Phagocytosis of β-1,3-D-Glucan-Derivatized Microbeads by Mouse Peritoneal Macrophages Involves Three Different Receptors," *Scand. J. Immunol.*, 1991; 33:297-306.
Maheshwari et al., "Immunoprotection by β-1,3 Glucan Antigen Combination in *Plasmodium berghei* Infection in Mice," *Indian J. Med. Res.*, Nov. 1989; 89:396-403.
Meira et al., "The Use of Glucan as Immunostimulant in the Treatment of Paracoccidioidomycosis," *Am. J. Trop. Med. Hyg.*, Nov. 1996; 55(5):496-503.
Pedroso, M., "Application of β-1,3-Glucan to Prevent Shipping Fever in Imported Heifers," *Arch. Med. Res.*, 1994 Summer; 25(2):181.
Rasmussen et al., "Dynamics of Blood Components and Peritoneal Fluid During Treatment of Murine *E. coli* Sepsis with β-1,3-D-Polyglucose Derivatives. I. Cells," *Scand. J. Immunol.*, 1990; 32:321-331.
Rasmussen et al., "Dynamics of Blood Components and Peritoneal Fluid During Treatment of Murine *E. coli* Sepsis with β-1,3-D-Polyglucose Derivatives. II. Interleukin 1, Tumour Necrosis Factor, Prostaglandin E2, and Leukotriene B4," *Scand. J. Immunol.*, 1990; 32:333-40.
Rasmussen et al., "Novel Immunomodulators with Pronounced In Vivo Effects Caused by Stimulation of Cytokine Release," *J. Cell Biochem.*, 1991; 46:60-68.
Sakagami et al., "Macrophage Stimulation Activity of Antimicrobial N,N-Dimethylaminoethyl Paramylon," in vivo, 1991; 5:101-105.
Seljelid et al., "In vivo Activation of Mouse Macrophages with β-1,3-D-Glucan Derivatized Plastic Beads," *Scand. J. Immunol.*, 1985; 21:601-605.
Seljelid et al., "The Protective Effect of β1 -3D-Glucan-Derivatized Plastic Beads Against *Eschericia coli* Infection in Mice," *Scand. J. Immunol.*,1987;25(1):55-60.
Seljelid et al., "Biological Effects of the Immunomodulator β1-3D Polyglucose are Strongly Potentiated by Conjugation to Biodegradable Microbeads," *Scand. J. Immunol.*, Jun. 1997; 45:683-687.
Song et al., "Yeast Glucan and Immunotherapy of Infectious Diseases," *Lysosomes in Applied Biology and Therapeutics 6*, Amsterdam, The Netherlands 1979; pp. 533-547.
Song et al., "Glucan-Induced Disease Resistance in Tiger Shrimp (*Penaeus monodon*)," *Dev. Biol. Stand.*, 1997; 90:413-421.
Williams et al., "Glucan Immunomodulation in Experimental *E. coli* Sepsis," *Adv. Exp. Med. Biol.*, 1982; 155:701-706.
Williams et al., "Immunotherapeutic Modification of *Escherichia coli*-Induced Experimental Peritonitis and Bacteremia by Glucan," *Surgery*, Mar. 1983; 93(3):448-454.
Williams et al., "Effect of Glucan on Neutrophil Dynamics and Immune Function in *Escherichia coli* Peritonitis," *J. Surg. Res.*, 1988; 44:54-61.
Williams et al., "The Role of Complement in Glucan-Induced Protection Against Septic Shock," *Circ. Shock*, 1988; 25(1):53-60.
Williams et al., "Immunization Against *Trypanosoma cruzi*: Adjuvant Effect of Glucan," *Int. J. Immunopharmacol.*, 1989; 11(4):403-410.
Zunft et al., "Influence of Nutrition on Resistance to Infections," *Die Nahrung*, 1976; 20(5):543-565. German.

* cited by examiner

* p=0.00021
**p=0.00038

Days Post-Infection

USE OF BETA-GLUCANS AGAINST BIOLOGICAL WARFARE WEAPONS AND PATHOGENS INCLUDING ANTHRAX

CROSS REFERENCE TO RELATED APPLICATIONS

This application is a continuation application of Ser. No. 10/268,201 filed Oct. 9, 2002 and is entitled to the benefit of Provisional Patent Application No. 60/328,206 entitled "Use of Beta Right™ Betafectin® and Whole Glucan Particles Beta-Glucans for the Prevention and Treatment of Pathogens including Biological Warfare Pathogens," filed Oct. 9, 2001, each of which is incorporated herein by reference.

FIELD OF THE INVENTION

The present invention relates to the prophylaxis or treatment of injury from biological warfare weapons, and more particularly, to the prophylaxis or treatment of infection by pathogenic organisms such as anthrax.

BACKGROUND OF THE INVENTION

One of the potential biological warfare agents most feared by civil defense planners today is *Bacillus anthracis*, or anthrax. This organism makes an effective bioterrorist weapon because it has a high mortality rate, can be readily prepared and stored as spore particles, and delivered over a large area as an aerosol. Thomas V. Inglesby et al., "Anthrax as a biological weapon: Medical and Public Health Management." JAMA, 281 (18) 1735-1745 (1999). This has caused anthrax to be classified as a category A (high priority) agent by the US Centers for Disease Control and Prevention (CDC).

Dissemination of biological warfare agents may occur by aerosol sprays, explosives, or food or water contamination. To be an effective biological weapon, airborne pathogens must be dispersed as fine particles less than 5 μm in size. Advanced delivery systems are not required for the aerosolized delivery of biological agents, which can be delivery by agricultural crop-dusters, aerosol generators on small boats or trucks, backpack sprayers, and even purse-sized perfume atomizers. A biological weapon attack is likely to be covert, and protective measures should be taken when warning is received or once there is suspicion that a biological warfare agent has been or soon will be used. Use of broad spectrum antibiotics is recommended by the CDC for suspected victims of a biological warfare attack, prior to the identification of the specific biological warfare agent used.

The CDC has three categories for biological warfare agents. Category A biological warfare agents are the most serious. The U.S. public health system and primary healthcare providers must be most prepared to address these biological agents, which include pathogens that are rarely seen in the United States. High-priority, Category A agents include organisms that pose a risk to national security because they can be easily disseminated or transmitted person-to-person, cause high mortality, with potential for major public health impact, might cause public panic and social disruption, and require special action for public health preparedness. These agents/diseases include: *Bacillus anthracis* (anthrax), *Clostridium botulinum* toxin (botulism), *Yersinia pestis* (plague), *Variola major* (smallpox), *Francisella tularensis* (tularemia), and viral hemorrhagic fevers.

Next are Category B biological warfare agents. These are the second highest priority agents, and include those that are moderately easy to disseminate, cause moderate morbidity and low mortality, and require specific enhancements of CDC's diagnostic capacity and enhanced disease surveillance. These agents/diseases include: *Coxiella burnetti* (Q fever), *Brucella* species (brucellosis), *Burkholderia mallei* (glanders), ricin toxin from *Ricinus communis* (castor beans), the epsilon toxin of *Clostridium perfringens*, and *Staphylococcus* enterotoxin B.

Finally, there are Category C biological warfare agents. These are the third highest priority agents, and include emerging pathogens that could be engineered for mass dissemination in the future because of availability, ease of production and dissemination, and potential for high morbidity, mortality, and major health impact. These agents/diseases include: Nipah virus, the hantaviruses, the tickborne hemorrhagic fever viruses, the tickborne encephalitis viruses, yellow fever, and *Mycobacterium tuberculosis* (tuberculosis).

An example of a Category A biological warfare agent is *B. anthracis*. *B. anthracis* is an aerobic gram-positive rod that commonly infects herbivores causing a serious and often fatal disease. Spores are produced at temperatures below 30° C. in soil and on inanimate objects, but not in living tissues. Spores can resist to temperatures above 100° C. for limited periods of time, making them highly persistent. Humans can acquire the disease by contact with infected animals or infected animal products. Once inside the body, spores germinate into "vegetative" or actively dividing cells. Direct contact between spores or infected tissues and broken skin results in cutaneous anthrax. Within two to five days of exposure, a small papule develops, followed by a necrotic ulcer surrounded by oedema. Death following treatment is very rare but untreated persons have a mortality rate near 20%. Ingestion of undercooked meat may result in gastrointestinal anthrax. Nausea, vomiting, and gastrointestinal bleeding ensue within 12 to 18 hours, leading to haemorrhagic lymphadenitis. Spread to the bloodstream and subsequent death can occur.

Inhalation anthrax is the most likely form of the disease from biological warfare use, and is the most dangerous. Much of the currently available data on human reaction to inhalation anthrax is a result of the accidental aerosolized release of anthrax spores from a military microbiology facility in Sverdlovsk in the former Soviet Union in 1979, which resulting in at least 79 cases of anthrax infection and 68 deaths. Inhalation of anthrax spores causes the most serious form of infection, resulting in influenza-like illness within one to five days of exposure. Early diagnosis of inhalational anthrax is difficult and requires a high index of suspicion, as the first stage of the disease is relatively benign. The second stage develops abruptly, however, with sudden fever, dyspnea, diaphoresis, and shock, leading to massive lymphadenopathy and hemorrhagic meningitis. In the second stage of illness, cyanosis and hypotension progress rapidly; death sometimes occurs within hours. Franz D. R., et al., "Clinical recognition and management of patients exposed to biological warfare agents." JAMA, 278, 399-411 (1997). Inhaled anthrax is nearly always fatal because of the rapid progression of the disease and the benign appearance of the initial symptoms. Fritz et al., Lab. Invest., 73, 691-702 (1995).

The pathogenesis of infection by *B. anthracis* is not yet completely understood. At its most basic level, extensive replication in the blood is generally what kills patients who succumb to anthrax. *B. anthracis*'s ability to expand so successfully derives partially from its production of virulence factors that can profoundly depress the immune system. The major virulence factors of *B. anthracis* are a poly-D-glutamic acid capsule, that inhibits ingestion and destruction by the immune system's macrophages and neutrophils, and exotoxin. Exotoxin is composed of three protein components;

protective antigen (PA), lethal factor (LF), and edema factor (EF). Ballard et al., PNAS, 93, 12531-12534 (1996). These proteins cooperate but are not always joined together. Protective antigen binds to cell surfaces to trigger the formation of an endosome which is used to transport edema factor and lethal factor across the endosomal membrane into the cytosol of the target cell. Edema factor upsets the controls on ion and water flow across the cell membrane, promoting swelling. Lethal factor is a protease whose precise mechanism of action remains unknown. Brossier et al., Infect. Immun., 68, 1781-1786 (2000). However, it is known that lethal toxin inhibits macrophages from releasing the immune messengers interleukin-1 (IL-1), interleukin-2 (IL-2), gamma interferon, and tumor necrosis factor alpha (TNF-α).

The macrophage plays a key role in the success or failure of many pathogenic organisms utilized as biological warfare agents, such as *B. anthracis*. Macrophages are the first cells to interact with *B. anthracis* via phagocytosis. Vesicles derived from the phagosomal compartment of alveolar macrophage are the primary sites of spore germination in a murine inhalation model. Guidi-Rontani et al., Mol Microbiol., 31, 9-17 (1999). Macrophages induce host defense responses such as cytokine secretion and cell mediated cytotoxicity against infection by pathogens such as anthrax. The early onset of toxin gene expression after germination is a key determinant in the macrophage response. The LF protein is lytic for macrophages and sublytic doses of LF cause a reduction of nitric oxide (NO) and tumour necrosis factor (TNF) production. Pellizzari et al., FEBS Letters, 462, 199-204 (1999). On the other hand, Hanna et al showed that sublytic concentration of LF could increase the production of IL-1 by activated macrophages. Hanna, et al., PNAS, 90, 10198-10201 (1993). Along with macrophage activation, Natural Killer (NK) and T cells also take an active part in protection against diseases such as anthrax. After first contact with antigen, a rise in the NK cell activity is observed, followed by its pronounced suppression. Soloklin et al., Zhurnal Mikrobiologii Epi. Immuno., 5, 72-76 (1995). The use of protective antibody against pathogens such as anthrax increases the duration of NK cell activity. This suggests a major role of macrophages and NK cells in the host defense mechanisms against biological warfare agents such as anthrax.

On a separate subject, β-glucan is a complex carbohydrate which has shown potential as an immunomodulator. It is generally derived from several sources, including yeast, bacteria, fungi and cereal grains. These sources provide β-glucans in a variety of mixtures and purities, and with a variety of different chemical structures. The structural diversity of β-glucans results from the fact that glucose molecules can be linked together in many different ways, resulting in compounds with different physical properties. For example, β(1,3)-glucans derived from bacterial and algae are linear, making them useful as a food thickener. Lentinan (from *Lentinus edodes*, Basidiomycete family) is a high MW β-glucan with single glucose branches linked (1,6)-β off of the (1,3) backbone every three residues. Schizophyllan (from *Schizophyllum commune*, Basidiomyctes family) is a similar β-glucan. Beta-glucans from barley, oat, or wheat have mixed (1,3)- and (1,4)β-linkage in the backbone, but no (1,6)-βbranches, and are generally of high molecular weight. The frequency of side chains, known as the degree of substitution or branching frequency, regulates secondary structure and solubility. Beta-glucans derived from yeasts have a backbone chain of β(1-3) linked glucose units with a low degree of inter and intra-molecular branching through β(1-6) linkages. Based on extensive published research it is widely accepted that baker's yeast (*Saccharomyces cerevisiae*) is a preferred source of β(1,3)-glucan, based on the purity and activity of the product obtained.

The cell wall of *S. cerevisiae* is mainly composed of β-glucans, which are responsible for its shape and mechanical strength. While best known for its use as a food grade organism, yeast is also used as a source of zymosan, a crude insoluble extract used to stimulate a non-specific immune response. Yeast zymosan serves as a rich source of β(1,3)-glucan. Yeast-derived β(1,3)-glucan appears to stimulate the immune system, in part by activating the innate immune system as part of the body's basic defense against fungal infections. Yeast β(1,3)-glucan is a polysaccharide composed primarily of β(1-3)-linked glucose molecules with periodic β(1-3) branches linked via β(1-6) linkages and is more formally known as poly-(1,6)-β-D-glucopyranosyl-(1,3)β-D-glucopyranose.

Various forms of β(1,3)-glucan have been prepared, with differing properties. These different forms vary in terms of their purity, particle size, and solubility. One of the larger and less soluble forms of β-glucan are whole glucan particles. Whole glucan particles are the remnants of the yeast cell wall prepared by separating growing yeast from its growth medium and subjecting the intact cell walls of the yeast to alkali, and removing unwanted proteins and nucleic acid material, as well as the mannan component of the cell wall. Normally, what remains is purified, 2-5 micron, spherical β-glucan particle. Whole glucan particles may be obtained from any glucan-containing fungal cell wall source, but the preferred source is *S. cerevisiae*. Methods of producing whole glucan particles are known in the art and are disclosed in U.S. Pat. Nos. 4,810,646, 4,992,540, 5,037,972, 5,082,936, 5,250,436, and 5,506,124, the contents of which are incorporated herein by reference.

Another, more processed form of β(1,3)-glucan is PGG glucan, which is an abbreviation of the full chemical name, poly-(1,6)-β-D-glucopyranosyl (1,3)β-D-glucopyranose. PGG glucan (PGG), in a particular formulation in saline, goes by the trademark Betafectin®. Generally, neutral underivatized β(1,3)-glucans are not soluble in physiological media due to their tendency to form tightly associated triple helix fibrils which resist hydration. PGG is prepared from whole glucan particles through a series of acid, alkaline and neutral treatment steps to yield a conformationally pure, triple helical soluble glucan preparation which can be maintained in a clear solution at neutral pH. Methods of producing PGG are known in the art and are disclosed in U.S. Pat. Nos. 5,322,841, 5,811,542, 5,663,324, 5,633,369, and 5,817,643, the contents of which are incorporated herein by reference. The soluble glucans produced by this process are branched polymers of glucose, containing β(1-3) and β(1-6) linkages in varying ratios depending on the source organism and the exact processing conditions used. The average weight of PGG-glucan molecules is generally about 5,000 to 500,000 daltons.

Microparticulate glucan is glucan that is refined to produce smaller fragments of whole glucan particle. Methods of producing microparticulate β-glucan are disclosed in U.S. Pat. Nos. 5,223,491, 5,397,773, 5,576,015, 5,702,719, and 5,705,184, the contents of which are incorporated herein by reference. The beta (1,3) glucan used to prepare microparticulate glucan is isolated from yeast cell walls by conventional methods known by those of ordinary skill in the art. Microparticulate glucan generally has average particle size is preferably about 1.0 microns or less, and more preferably about 0.20 microns or less.

Beta glucans possess a diverse range of activities. The ability of β-glucan to increase nonspecific immunity and resistance to infection is similar to that of endotoxin. Early studies on the effects of (β(1,3)-glucan on the immune system focused on mice. Subsequent studies demonstrated that β(1, 3)-glucan has strong immunostimulating activity in a wide variety of other species, including earthworms, shrimp, fish, chicken, rats, rabbits, guinea pigs, sheep, pigs, cattle, and humans. For a review, see Vetvicka V. "β-glucans as immunomodulators", JAMA, 3, 24-31 (2001). Based on these studies it has been concluded that β(1,3)-glucan represents a type of immunostimulant that is active across the evolutionary spectrum, likely representing an evolutionarily-conserved innate immune response directed against fungal pathogens. However, despite extensive investigation, no consensus has been achieved on the source, size, and form of β(1,3)-glucan ideal for use as an immunostimulant.

There have been several studies on the use of β-glucans to prevent infection, primarily in the context of surgical sepsis. For example, Williams et al. assessed the role of combined immunomodulation with β-glucan and antibiotic (gentamycin) in the treatment of experimental sepsis. Williams et al., "Synergistic effect of nonspecific immunostimulation and antibiotics in experimental peritonitis" Surgery, 102(2), 208-14 (1987). This particular study noted that β-glucan treatment alone after $E.\ coli$ inoculation was expected to have no beneficial effect on long-term survival. A similar study was conducted by Kaiser, who used PGG glucan and cefazolin antibiotic synergistically to prevent staphylococcal wound infection. Kaiser A. B, Kemodle D. S., "Synergism between poly-(1-6)-beta-D-glucopyranosyl-(1-3)-beta-D-glucopyranose glucan and cefazolin in prophylaxis of staphylococcal wound infection in a guinea pig model", Antimicrob. Agents Chemother., 42(9), 2449-51 (1998).

The molecular mechanism of action of β-glucan appears to involve specific β-glucan receptor binding sites on the cell membranes of immune cells such as neutrophils and macrophages. Mannans, galactans, α(1-4)-linked glucose polymers and β(1-4)-linked glucose polymers have no avidity for this receptor. Recent data suggests that CR3, the receptor for C3 complement protein, serves as a major receptor for β-glucans. Ligand binding to the β-glucan receptor results in complement activation, phagocytosis, lysosomal enzyme release, and prostaglandin, thromboxane and leukotriene generation providing a more functionalized innate immune system to protect against a wide array of pathogenic challenges.

The recent increased threat of bioterrorism, which could result in the widespread dissemination of one or more pathogenic organisms, has increased our awareness that we have relatively few prevention and treatment options available for protecting the U.S. public. In 1970, a World Health Organization (WHO) expert committee estimated that the release of 50 kg of anthrax from an aircraft over a developed urban population of 5 million would result in 250,000 casualties, 100,000 of whom could be expected to die without treatment. Health Aspects of Chemical and Biological Weapons, Geneva, Switzerland, WHO; 98-99 (1970). A 1993 report by the US Congressional Office of Technology Assessment estimated that between 130,000 and 3,000,000 deaths would follow from the aerosolized release of 100 kg of anthrax spores upwind of the Washington, D.C. area—lethality matching or exceeding that resulting from the detonation of a hydrogen bomb. Office of Technology Assessment, US Congress, Washington, D.C., "Proliferation of Weapons of Mass Destruction", US Government Printing Office, 53-55 (1993).

The first evidence of a terrorist release of anthrax as a biological weapon would likely be patients seeking medical treatment for symptoms of inhalational anthrax. The sudden appearance of a large number of patients in a city or region with an acute-onset flu-like illness and fatality rates of 80% or more, with nearly half of all deaths occurring within 24-48 hours, would indicate the highly likelihood of an anthrax or pneumonic plague release. Rapid diagnostic tests for diagnosing anthrax, such as enzyme-linked immunosorbent assay for protective antigen and polymerase chain reaction, are available only at national reference laboratories. Many other biological warfare agents would be equally difficult to respond to in a timely fashion.

Conventional anti-microbial therapies, such as antibiotics, can be useful to treat some bioterroristic pathogens, but are generally not useful for protecting the public from infection until after exposure. Antibiotics such as ciprofloxacin (a fluoroquinolone antibiotic) and doxycycline (a tetracycline antibiotic) are useful for treating anthrax; however, even the use of multiple antibiotics is often not enough to prevent symptomatic patients from succumbing to infection. Furthermore, reports have been published of a $B.\ anthracis$ strain that has been engineering by Russian scientists to resist antibiotics. Prophylactic administration of vaccines, such as that disclosed by Ivies et al. in U.S. Pat. No. 6,387,665, provides another means to protect the public from infection. For example, a US anthrax vaccine, made up of an inactivated cell-free product, has been mandated for all US military active- and reserve-duty personnel. Unfortunately, a single vaccine is only able to protect against infection by a single microorganism and does not provide broad protection against multiple possible pathogenic terrorist threats. Further, widespread vaccination is not recommended for protecting the general public as there is limited availability of vaccine, and debate as to whether the risk of adverse side-effects justifies its general use. The timeframe for the development of safe and effective treatment and providing cost-effective delivery of these treatments to a large military or civilian population are also significant issues. Thus, what is clearly needed is a method of protecting against biological warfare which increases survival when administered both before and after exposure, and which provides effective defense against a wide variety of possible biological warfare agents, as well as being inexpensive to provide to the general public, and readily capable of being stored for extended periods.

SUMMARY OF THE INVENTION

The present invention provides a strategy to broadly protect the military and the public from injury from biological warfare weapons, particularly infective agents such as anthrax. Applicant has discovered the manner in which β-glucans, particularly whole glucan particles, PGG glucan, and microparticulate glucan, provide an excellent means of providing defense against biological warfare weapons as they provide general immune enhancement, thus providing an increased defense against a wide variety of biological threats. Furthermore, β(1,3)-glucan is readily stored as it is both pharmaceutically stable and relatively compact, making it easy to hold in reserve for use in case of a threatened or suspected biological warfare attack. Beta (1,3)-glucan can also be used without significant side effects, making it more readily usable in situations where it is uncertain whether or not a biological attack or natural infectious outbreak has occurred. Finally, β(1,3)-glucan can enhance the effectiveness of other medical countermeasures such a vaccines and antibiotics, in addition to being effective when used alone. The ability of β(1,3)-glucan administration to increase survival time suggests that immunomodulator intervention can also provide time for other antimicrobial therapies to be initiated.

The use of β-glucan to broadly protect the public from infection by a wide range of pathogenic microorganisms such as anthrax takes advantage of β-glucan's enhancement of the immune system. The use of β-glucan either as a prophylactic before exposure and/or as part of a treatment regimen following exposure provides two strategies that protects the public after exposure to a pathogenic challenge. Use of β-glucan as an immunomodulator can also enhance the effectiveness of other medical countermeasures such as vaccines, immune sera, and/or antibiotics.

The anti-infective activity of β(1,3)-glucan is mediated through the stimulation of the microbicidal activity of white blood cells, mainly monocytes, macrophages, neutrophils, and NK cells of the innate immune system. While not intending to be limited by theory, this immune stimulation appears to occur through two different mechanisms. First, monocytes, macrophages, neutrophils and NK cells become primed for cytotoxic activity upon β(1,3)-glucan binding to complement receptor type 3 (CR3) on their cell surface. Activation of CR3 requires both binding to iC3b (a complement protein) and binding to a secondary stimulus, such as β(1,3)-glucan. Since bacteria such as anthrax lack β(1,3)-glucan, providing this polysaccharide facilitates a heightened innate immune response to foreign substances opsonized with iC3b. Second, β(1,3)-glucan binding can crosslink glycolipid receptors present on the membranes of various white blood cells, initiating a cascade of cellular responses. Early events, such as $Ca^{2+}$ influx mediated by protein kinase C and activation of transcription factors, leads to an overall heightened immune response. These responses include proliferation of immune cells as well as the release of various cytokines such as IL-1, IL-2, and TNF-α. Activation of macrophages is particularly important, as they are a crucial first line of defense against foreign substances and are suppressed by *B. anthracis* exotoxin.

Both systemically and orally administered β(1,3)-glucans significantly increase the survival of animals exposed to pathogens such as anthrax. For example, reported expected survival rates of people exposed to lethal airborne dosages of anthrax are only 20-30% using traditional therapies. However, the present invention provides a potential survival rate of >80% using whole glucan particles or PGG-glucan. Specifically, the use of β(1,3)-glucan increased the survival rate of infected test animals from 30% to 80%, prolonged the survival time of animals lethally infected with anthrax by 2.5 days, diminished the bacterial load in the organs of surviving infected animals, and increased the proportion of bacteria-free animals.

In summary, the present invention provides a method of preventing injury from biological warfare agents in humans or animals by administering a prophylactically or therapeutically effective amount of β(1,3)-glucan. In a preferred embodiment, the invention provides a method of treating or preventing pathogenesis of infection in humans or animals by one or more infectious agents by administering a prophylactically or therapeutically effective amount of β(1,3)-glucan. Preferably, the β(1,3)-glucan used is PGG-glucan, whole glucan particles, microparticulate glucan, or a combination thereof. The β(1,3)-glucan may be administered orally, topically, subcutaneously, intramuscularly, transdermally, intradermally, intravenously, or through the gastrointestinal tract.

Beta glucan is preferably administered, either before or after exposure to infection, in amounts from about 0.1 mg/Kg to about 100 mg/Kg of PGG glucan or about 0.1 mg/Kg to about 500 mg/Kg of whole glucan particles, or a combination thereof. More preferably, β-glucan is administered in amounts from about 1 mg/Kg to about 10 mg/Kg of PGG glucan or about 2 mg/Kg to about 20 mg/Kg of whole glucan particles, or a combination thereof.

The present invention provides potent prevention or treatment of infection by the type of infectious agents expected to be used by bioterrorists. These infectious agents include agents such as those listed as category A, B, and C biological warfare agents by the CDC. Such infectious agents include, but are not limited to, *B. anthracis* (anthrax), Brucellosis, *Burkholderia mallei* (glanders), Cholera, *Clostridium Perfringens* Toxins, Congo-Crimean Hemorrhagic Fever, Ebola Haemorrhagic Fever, Melioidosis, Plague *Yersinia pestis*, Q Fever, Ricin, Rift Valley Fever, Saxitoxin, Smallpox, Staphylococcal Enterotoxin B, Trichothecene Mycotoxins, Tularemia, Venezuelan Equine Encephalitis, Viral Hemorrhagic fever, Nipah virus, Hantaviruses, yellow fever, multidrug-resistant tuberculosis, Marburg Virus and Dengue Virus. In a preferred embodiment, the present invention provides a method of treating and preventing infection of humans and animals by *B. anthracis*. Additionally, whole glucan particles, PGG-glucan, and microparticulate glucan have the potential to provide a potent immunomodulator treatment to prevent or treat infections caused by infectious agents that may not be attributed to bioterrorists, including infectious agents that may be drug resistant and/or drug sensitive.

In addition to providing a method of treating and preventing infection, the present invention also provides a method of preventing injury from biological warfare agents in humans or animals by administering a prophylactically or therapeutically effective amount of β(1,3)-Glucan. Amounts of β-glucan used in preferred embodiments are the same as those listed above for use in preventing infection. In alternate embodiments, the present invention also provides methods of preventing injury from biological warfare agents in humans or animals by administering a prophylactically or therapeutically effective amount of a synergistic combination of β(1,3)-Glucan and antibiotic, or by delivering an effective amount of β(1,3)-Glucan subsequent to vaccination against biological warfare agents or treatment with immune sera or monoclonal antibodies against said biological warfare agents.

Finally, the present invention provides a compact composition of β-glucan which is stable in storage for at least two years at room temperature. In a preferred embodiment, the β-glucan used for this stable, compact composition is whole glucan particle which comprises about 80% of the mass of the composition used. The availability of a stable anti-infective agent helps make β-glucan ideal for stockpiling for use against a potential bioterrorist attack.

DETAILED DESCRIPTION OF THE INVENTION

Figure 1:
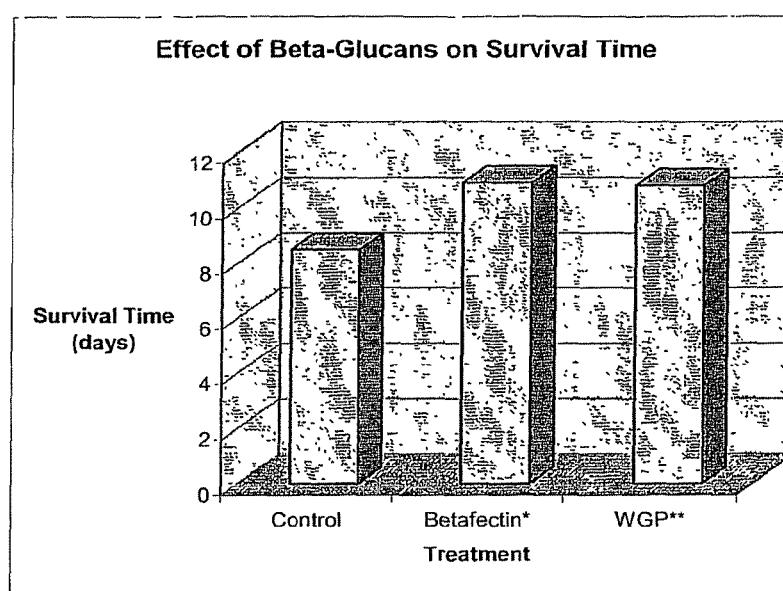
FIG. 1 is a graph showing the effect of β-glucan on survival time after exposure to anthrax.
Figure 2:
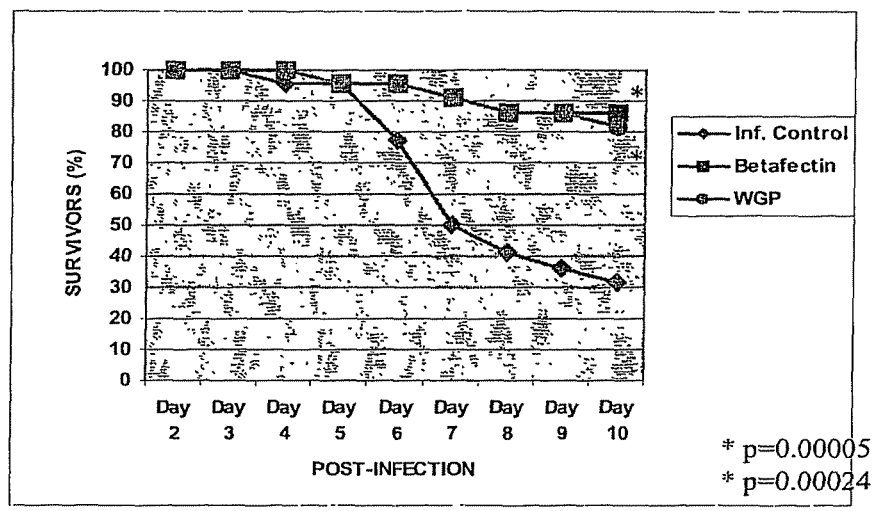
FIG. 2 is a graph showing the percent of survivors during anthrax infection in mice treated with β-glucan.
Figure 3:
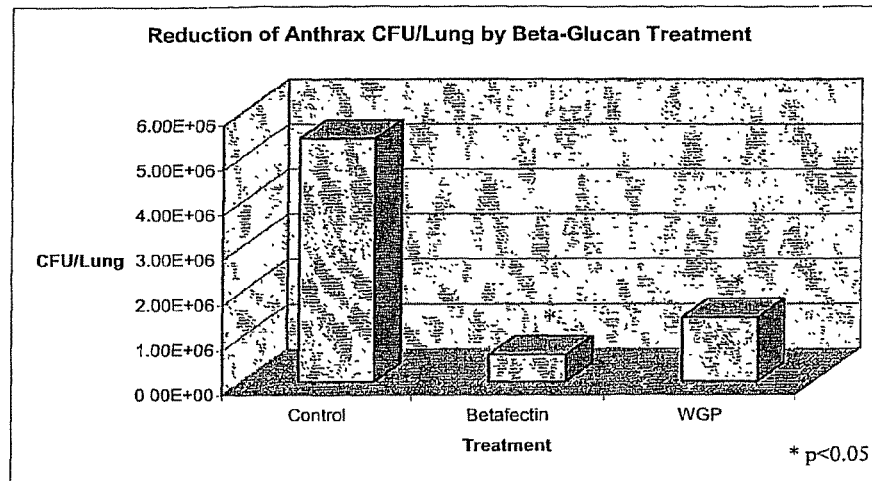
FIG. 3 is a graph showing the reduction of anthrax CFUs in the lung after β-glucan treatment.
Figure 4:
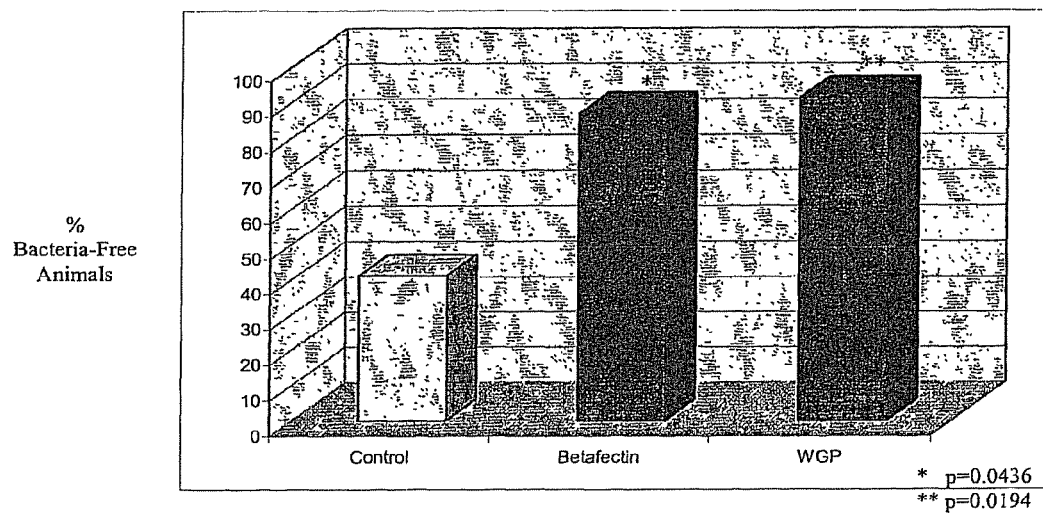
FIG. 4 is a graph of the effect of β-glucan on the percentage of bacteria-free animals.

The present invention provides methods and compositions for prophylaxis or treatment of infection following exposure to pathogens such as those used in biological warfare. In a preferred embodiment, the present invention provides methods and compositions for the prophylaxis or treatment of infection following exposure to *B. anthracis*, also known as anthrax.

The anti-infective provided by βglucan of the present invention is a useful strategy for broadly protecting the military and the public from infection by pathogens such as those used in biological warfare. The compositions of the present invention include β-glucan. More specifically, the compositions of the present invention comprise whole glucan particles, PGG-glucan, microparticulate glucan, and combinations thereof. PGG (poly-1-6-β-D-glucopyranosyl-1-3-β-D-glucopyranose) is a highly purified soluble glucose polymer prepared by acid hydrolysis from whole glucan particles. The β-glucan compositions may also include an optional carrier, excipient, and/or adjuvant. It has been found that the compositions of the present invention, which include one or more of the previously mentioned forms of β-glucan, significantly increase the survival of infected animals, including those infected with anthrax.

The structure-function properties of the β-glucan preparation depend on the source from which it is obtained. The source of β-glucan can be yeast or other fungi, or any other source containing glucan having the properties described herein. Yeast cells are a preferred source of glucans. The yeast strains employed in the present process can be any strain of yeast, including, for example, *S. cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P ohmeri, Torulopsis bovina,* and *T. glabrata.*

Yeast cells may be produced by methods known in the art. Typical growth media comprise, for example, glucose, peptone and a yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid-to-late logarithmic phase of growth, to minimize the amount of glycogen and chitin in the yeast cells.

As previously suggested, two forms of Beta (1,3)-glucans utilized in the present invention include an insoluble particle whole glucan particle, and a soluble product, PGG-glucan (PGG). Whole glucan particles can be purified from baker's yeast cell walls following extraction of cellular proteins, nucleic acids, lipids, and most non-glucose based oligosaccharides. What remains is a highly purified, 2-10 micron spherical β(1,3)-glucan particle, which maintains the glucans intact three dimensional in vivo morphology from the cells from which they are derived.

PGG (poly-(1,6)β-D-glucopyranosyl-(1,3)β-D-glucopyranose) is a highly purified soluble glucose polymer prepared by acid hydrolysis of whole glucan particles. The preparation of both forms of β-glucan are described below. Yeast is the preferred source of β(1,3)-glucan, but other sources which also produce β(1,3)-glucan are contemplated within the scope of the present invention.

Microparticulate glucan represents another embodiment of the present invention. Generally, the β(1,3) glucan used to prepare microparticulate glucan is isolated from yeast cell walls by conventional methods known by those of ordinary skill in the art and processed to produce microparticulate β-glucan. Microparticulate glucan generally has average particle size is preferably about 1.0 microns or less, and more preferably about 0.20 microns or less. It is noted that compositions may include one or more of the various forms described herein.

The preparation of whole glucan particles is described in U.S. Pat. Nos. 4,810,646, 4,992,540, 5,037,972, 5,082,936, 5,028,703, 5,250,436, and 5,506,124, the disclosures of which are incorporated herein by reference. This process yields a product which maintains the morphological and structural properties of the glucan as found in vivo and will be referred to as a whole glucan, or whole glucan particles.

Preparation of Whole Glucan Particles Involves Treating the Yeast with an Aqueous Alkaline solution at a suitable concentration to solubilize a portion of the yeast and form alkali-hydroxide-insoluble whole glucan particles having primarily β(1-6) and β(1-3) linkages. The alkali generally employed is an alkali-metal hydroxide, such as sodium or potassium hydroxide. Preferably, the starting material consists essentially of yeast separated from the growth medium. It is more difficult to control consumption of the aqueous hydroxide reactants and the concentration of reactants in the preferred ranges when starting with yeast compositions that are less concentrated. It is noted that the structure-function properties of the whole glucan preparation depend on the source from which it is obtained. The source of whole glucan can be yeast or other fungi, or any other source containing glucan having the properties described herein. However, yeast cells are a preferred source of glucans. The yeast should have intact, unruptured cell walls since the preferred properties of the instant whole glucan particles depend upon an intact cell wall.

The treating step is performed by extracting the yeast in the aqueous hydroxide solution. The intracellular components and mannoprotein portion of the cell are solubilized in the aqueous hydroxide solution, leaving insoluble cell wall material which is substantially devoid of protein and having a substantially unaltered three dimensional matrix of β(1-6) and β(1-3) linked glucan. The preferred conditions of performing this step result in the mannan component of the cell wall being dissolved in the aqueous hydroxide solution. The intracellular constituents are hydrolyzed and released into the soluble phase. Preferably, the conditions of digestion are such that at least in a major portion of the cells, the three dimensional matrix structure of the cell walls is not destroyed. More preferably, substantially all the cell wall glucan remains unaltered and intact.

The aqueous hydroxide digestion step is preferably carried out in a hydroxide solution having initial normality of from about 0.1 to about 10.0. Typical hydroxide solutions include hydroxides of the alkali metal group and alkaline earth metals of the Periodic Table. The preferred aqueous hydroxide solutions are of sodium and potassium, due to their availability. The digestion is preferably carried out at a temperature of from about 20° C. to about 121° C. with lower temperatures requiring longer digestion times. When sodium hydroxide is used as the aqueous hydroxide, the temperature is preferably from about 80° C. to about 100° C. and the solution has an initial normality of from about 0.75 to about 1.5. The hydroxide added is in excess of the amount required, thus, no subsequent additions are necessary.

Generally from about 10 grams to about 500 grams of dry yeast per liter of hydroxide solution is used. Preferably the aqueous hydroxide digestion step is carried out by a series of contacting steps so that the amount of residual contaminants such as proteins are less than if only one contacting step is utilized. In other words, it is desirable to remove substantially all of the protein material from the cell. Preferably such removal is carried out to such an extent that less than one percent of the protein remains with the insoluble cell wall glucan particles. An additional extraction step is preferably carried out in a mild acid solution having a pH of from about 2.0 to about 6.0. Typical mild acid solutions include hydrochloric acid, sodium chloride adjusted to the required pH with hydrochloric acid and acetate buffers. This extraction step is preferably carried out at a temperature of from about 20° C. to about 100° C. The digested glucan particles can be, if necessary, subjected to further washings and extraction to reduce the protein and contaminant level to the preferred amounts hereinbefore indicated.

By conducting this process without disrupting the cell walls, the extraction can be conducted at more severe conditions of pH and temperature than was possible with the prior art procedure which included a step of disrupting the cell walls. That is, the process of this invention avoids product degradation while employing these severe extraction conditions which permits elimination of time-consuming multiple extraction steps. After the aqueous hydroxide treatment step, the final whole glucan product comprises about 5 to about 30 percent of the initial weight of the yeast cell; preferably the product is from about 7 to about 15 percent by weight.

The whole glucan particles can be further processed and/or further purified, as desired. For example, the glucan can be dried to a fine powder (e.g., by drying in an oven, lyophilizing or spray drying); or can be treated with organic solvents (e.g., alcohols, ether, acetone, methyl ethyl ketone, chloroform) to remove any traces or organic-soluble material, or retreated with hydroxide solution, to remove additional proteins or other impurities which may be present.

The whole glucan particles obtained from the previously described process are comprised of highly pure glucan, which consists essentially of $\beta(1-6)$ and $\beta(1-3)$ linked glucan. Following processing, the whole glucan particles contain very little contamination from protein and glycogen. Preferably, the whole glucan particles are spherical in shape with a diameter of about 2 microns to about 10 microns and contain greater than 85% by weight hexose sugars, approximately 1% by weight protein and no detectable amount of mannan, as determined by Fourier Transform Infrared Spectroscopy. Glucans obtained by prior processes contain substantially higher quantities of chitin and glycogen than the present glucans.

A second chemical treatment may be used in which whole glucan particles are treated with an enzyme or an acid, to change the amount of $\beta(1-3)$ or $(1,6)$ linkages. For whole glucan particles derived from some yeast strains, enzyme treatment causes a decrease in the viscosity, and for others, it causes an increase in viscosity, but in general, alters the chemical and hydrodynamic properties of the resulting glucans. For example treatment with a glucanase enzyme, such as laminarinase, alters the $\beta(1-3)$ linkages which alters the hydrodynamic properties of the whole glucan particles in aqueous suspensions. Also for example, treatment with a mild acid, such as acetic acid, alters the $\beta(1-3)$ linkages which additionally alters the hydrodynamic properties of the whole glucan particles in aqueous suspensions. A description of this second chemical treatment is disclosed in U.S. Pat. Nos. 6,020,324 and 6,143,731.

The preparation of PGG-glucan is described in U.S. Pat. Nos. 5,322,841, 5,811,542, 5,663,324, 5,633,369, and 5,817,643, the disclosures of which are incorporated herein by reference. This method involves treating whole glucan particles with a series of acid and alkaline treatments to produce soluble glucan which forms a clear solution at a neutral pH. The whole glucan particles utilized in this present invention can be in the form of a dried powder, prepared by the process described above. For the purpose of this present invention it is not necessary to conduct the final organic extraction and wash steps.

In order to prepare PGG, whole glucan particles are suspended in an acid solution under conditions sufficient to dissolve the acid-soluble glucan portion. For most glucans, an acid solution having a pH of from about 1 to about 5 and a temperature of from about 20° to about 100° C. is sufficient. Preferably, the acid used is an organic acid capable of dissolving the acid-soluble glucan portion. Acetic acid, at concentrations of from about 0.1 to about 5M or formic acid at concentrations of from about 50% to 98% (w/v) are useful for this purpose. The treatment is preferably carried out at about 90° C. The treatment time may vary from about 1 hour to about 20 hours depending on the acid concentration, temperature and source of whole glucan particles. For example, modified glucans having more $\beta(1-6)$ branching than naturally-occurring, or wild-type glucans, require more stringent conditions, i.e., longer exposure times and higher temperatures. This acid-treatment step can be repeated under similar or variable conditions. Modified whole glucan particles from the strain, S. cerevisiae R4, which have a higher level of $\beta(1-6)$ branching than naturally-occurring glucans, can also be used. Treatment is carried out twice: first with 0.5M acetic acid at 90° C. for 3 hours and second with 0.5M acetic acid at 90° C. for 20 hours.

The acid-insoluble glucan particles are then separated from the solution by an appropriate separation technique, for example, by centrifugation or filtration. The pH of the resulting slurry is adjusted with an alkaline compound such as sodium hydroxide, to a pH of about 7 to about 14. The slurry is then re-suspended in hot alkali having a concentration and temperature sufficient to solubilize the glucan polymers. Alkaline compounds which can be used in this step include alkali-metal or alkali-earth metal hydroxides, such as sodium hydroxide or potassium hydroxide, having a concentration of from about 0.1 to about 10N. This step can be conducted at a temperature of from about 4° C. to about 121° C., preferably from about 20° C. to about 100° C. In one embodiment of the process, the conditions utilized are a 1N solution of sodium hydroxide at a temperature of about 80°-100° C. and a contact time of approximately 1-2 hours. The resulting mixture contains solubilized glucan molecules and particulate glucan residue and generally has a dark brown color due to oxidation of contaminating proteins and sugars. The particulate residue is removed from the mixture by an appropriate separation technique, e.g., centrifugation and/or filtration.

The resulting solution contains soluble glucan molecules. This solution can, optionally, be concentrated to effect a 5 to 10 fold concentration of the retentate soluble glucan fraction to obtain a soluble glucan concentration in the range of about 1 to 5 mg/ml. This step can be carried out by an appropriate concentration technique, for example, by ultrafiltration, utilizing membranes with nominal molecular weight levels (NMWL) or cut-offs in the range of about 1,000 to 100,000 daltons. A membrane cut-off of about 10,000 daltons is particularly useful for this step.

The concentrated fraction obtained after this step is enriched in the soluble, biologically active PGG. To obtain a pharmacologically acceptable solution, the glucan concentrate is further purified, for example, by diafiltration. In one embodiment of the present method, diafiltration is carried out using approximately 10 volumes of alkali in the range of about 0.2 to 0.4N. The preferred concentration of the soluble glucan after this step is from about 2 to about 5 mg/ml. The pH of the solution is adjusted in the range of about 7-9 with an acid, such as hydrochloric acid. Traces of proteinaceous material which may be present can be removed by contacting the resulting solution with a positively charged medium such as DEAE-cellulose, QAE-cellulose or Q-Sepharose. Proteinaceous material is detrimental to the quality of the glucan product, may produce a discoloration of the solution and aids in the formation of gel networks, thus limiting the solubility of the neutral glucan polymers. A clear solution is obtained after this step.

The highly purified, clear glucan solution can be further purified, for example, by diafiltration, using a pharmaceutically acceptable medium (e.g., sterile water for injection, phosphate-buffered saline (PBS), isotonic saline, dextrose) suitable for parenteral administration. The preferred membrane for this diafiltration step has a nominal molecular weight cut-off of about 10,000 daltons. The final concentration of the glucan solution is adjusted in the range of about 0.5 to 5 mg/ml. In accordance with pharmaceutical manufacturing standards for parenteral products, the solution can be terminally sterilized by filtration through a 0.22 μm filter. The soluble glucan preparation obtained by this process is sterile, non-antigenic, and essentially pyrogen-free, and can be stored at room temperature for extended periods of time without degradation.

Methods of producing microparticulate β-glucan are disclosed in U.S. Pat. Nos. 5,223,491, 5,397,773, 5,576,015, 5,702,719, and 5,705,184, the contents of which are incorporated herein by reference. In general, microparticulate β-glucan may be produced by isolating β(1,3) glucan and processing it to obtain small particle sizes. An example of a process for obtaining the desired smaller particle size of microparticulate glucan, includes the use of a blender or ball mill to grind the β(1,3) glucan into small particles. One grinding or particle size reduction method utilizes a blender having blunt blades, wherein the glucan mixture is blended for a sufficient amount of time, preferably several minutes, to completely grind the particles to the desired size without overheating the mixture. Another grinding method comprises grinding the glucan mixture in a ball mill with 10 mm stainless steel grinding balls. This latter grinding method is particularly preferred when a particle size of about 0.20 microns or less is desired.

Another form of β(1,3)-glucan is neutral soluble glucan. Neutral soluble glucan (NSG) is a term that describes a patented matter of composition related to PGG-glucan, but is a more generic term that covers all conformational forms of water soluble glucan. While PGG-glucan is typically a triple helix form of β-glucan, NSG generally refers to the single stranded helical form.

The composition administered in the method of the present invention can optionally include, in addition to whole glucan particles, PGG, microparticulate glucan or combinations thereof, other components, such as carriers, excipients, adjuvants and/or other beneficial active components. Such other beneficial active components may include the corresponding antibiotics for each of the previously-mentioned biological warfare pathogens. Other components included in a particular composition may be determined primarily by the manner in which the composition is to be administered. For example, a composition to be administered orally in table form can include, in addition to β-glucan, fillers (e.g. lactose), binders (e.g., carboxymethyl cellulose, gum Arabic, gelatin), adjuvants, flavoring agents, coloring agents, other active agents (e.g. pharmaceuticals, minerals, vitamins) and coating materials (e.g., wax or plasticizer). Additionally, compositions to be administered in liquid form may include whole glucan particles, PGG, microparticulate glucan or combinations thereof, and, optionally, emulsifying agents, flavoring agents and/or coloring agents. Also compositions including whole glucan particles, PGG, microparticulate glucan or combinations thereof, administered parenterally may be mixed, dissolved, or emulsified in water, sterile saline, PBS, dextrose, or other biologically acceptable carriers.

The mode of administration of the β-glucan preparation can be oral, enteral, topical, parenteral, intravenous, subcutaneous, intraperitoneal, intramuscular, or intranasal. However, oral administration of β(1,3)-glucans is a preferred embodiment of the present invention, as oral administration is both more convenient and less invasive. Furthermore, it has been found that oral administration is beneficial since it stimulates the innate immune system particularly when it comes in contact with macrophages present in Peyer's patches. Peyer's patches are specialized regions in the small intestine that transport antigens to the immune cells of the Gut-Associated-Lymphatic-Tissue (GALT). Activated macrophages travel to the GALT where they communicate the presence of a foreign antigen to other members of the immune system, resulting in the activation of other members of the innate immune system such as macrophages, neutrophils, and NK cells.

The form in which the composition will be administered (e.g., powder, table, capsule, solution, emulsion) will depend on the route by which it is administered. The quantity of the composition to be administered will be determined on an individual basis, and will be based at least in part on consideration of the severity of infection or injury in the patient, the patient's condition or overall health, the patient's weight, the time available before other treatment and the means of administration (e.g. a larger amount may be administered for oral compositions than for systemic compositions). In general, a single dose will normally contain approximately 0.01 mg to 500 mg of β-glucan per kilogram of body weight, preferably 1 mg to 250 mg of β-glucan per kilogram of body weight, more preferably 2 mg to 20 mg of β-glucan per kilogram of body weight.

Figure 7:
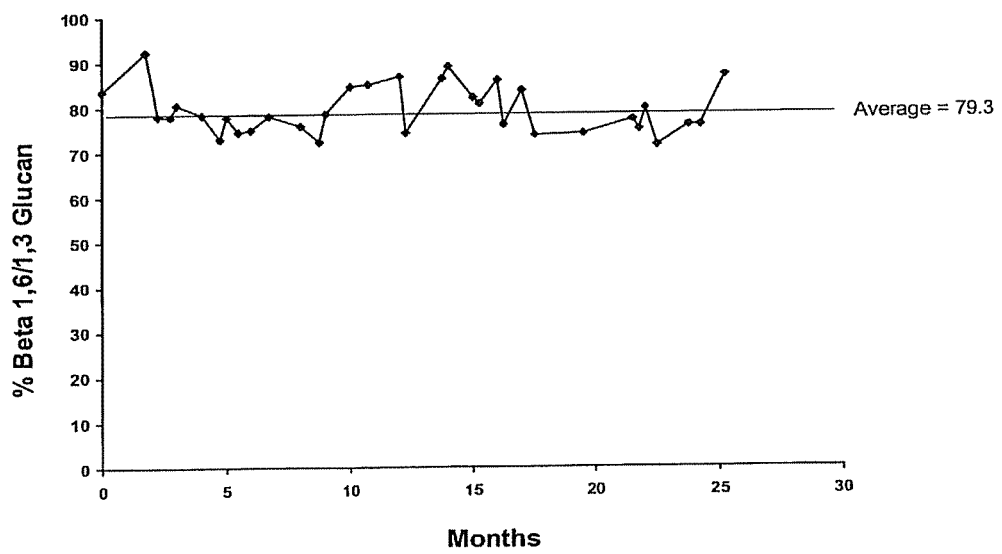
FIG. 7 is a graph of the stability of whole glucan particles at room temperature over a two year period.

The previously described forms of β-glucan of the present invention also have been found to remain stable over extended periods of time. Whole glucan particles can be stored as a pill at room temp and can be administered either orally, topically or systemically. PGG or NSG can be stored as a solution at room temperature and is usually administered systemically. Whole glucan particles and PGG are both stable for at least 2 years at 25° C. FIG. 7 depicts the results of a real time stability study done on Imucell™ WGP β-glucan stored at room temperature (25° C.) over a 25 months period. The composition of the sample was evaluated one per month, and showed no diminishment of the amount of active β-glucan present over the 25 month period. The average percentage of β-glucan present was 79.3%, with a standard deviation of 5.3.

To demonstrate the activities of β-glucan compositions against a potential biological weapon, a series of studies were carried out to show how PGG and whole glucan particles can enhance resistance against anthrax infection in a mouse model system. In the studies whole glucan particles (Imucell™ WGP Glucan) were purified from the cell walls of Baker's yeast and PGG was prepared by acid hydrolysis from whole glucan particles.

The prophylactic effects of systemic PGG or whole glucan particles on groups of mice which were subsequently exposed to *B. anthracis* spores was tested. All experiments were performed twice. Statistical analysis was performed on the two independent series of data. The results are shown in FIG. 1 which clearly demonstrates that a single dose of PGG (Betafectin; 2.5 mg/Kg) or 200 μg/mouse of whole glucan particles (10 mg/Kg) significantly increased survival time. In these experiments, the mean survival time for the control groups infected with anthrax was 8.4/8.5 days. The mean survival time significantly increased for the groups treated with PGG (10.2/11.5 days) and with whole glucan particles (10/11.5 days). Analysis of data pooled from the two experiments showed a statistically significant increase in the survival of PGG-treated mice (10.86 days) or whole glucan particles (10.80 days) when compared to control (8.45 days).

The anthrax-protective effects of systemic prophylactic treatment with β(1,3) glucan is shown in FIG. 2 which shows the percent of survivors during anthrax infection in mice treated with PGG or whole glucan particles. A single dose of PGG glucan (50 μg) or whole glucan particles (200 μg) or control saline was administered two days before lethal challenge with *B. anthracis*. The course of the infection was followed for a period of 10 days, and the number of survivors recorded daily. In these experiments, only 7 out of 22 control animals survived the observation period. In comparison, 19 out of the 22 PGG-treated mice and 18 of the 22 whole glucan particles-treated mice survived the same period of time.

The stimulation of the host innate antimicrobial immune response by PGG (Betafectin) and whole glucan particles resulted in enhanced microbial killing, as evidenced by a significantly reduced microbial bioburden in the lungs of treated animals shown in FIGS. 3 and 4. The results of these experiments demonstrate that a single dose of Betafectin (2.5 mg/Kg) or 200 μg/mouse of whole glucan particles (10 mg/Kg) significantly decreased the bacterial load in the lung, and increased the number of bacteria-free mice at the end of the observation period. The enhancement of the host immune response by β(1,3) glucans resulted in a significant percentage (>80%) of the surviving treated anthrax-challenged mice being bacteria-free by 10 days post-challenge, as seen by the relative absence of *B. anthracis* CFUs in the lung.

As previously indicated, oral administration of β(1,3)-glucans is a preferred embodiment of the present invention, as oral administration is both more convenient, less invasive, and leads to the stimulation of macrophages in the peyer's patch region. FIGS. 5A and 5B show the effect of a prophylactic oral whole glucan particles treatment regimen on mouse survival of a lethal anthrax challenge. The survival results shown in FIG. 5A demonstrate that daily oral prophylactic dosing of whole glucan particles (>2 mg/kg) significantly increased the number of anthrax survivors. In these experiments, only 5 out of 10 control animals survived the anthrax infection (50% survival). In comparison, animals treated prophylactically with daily oral doses of 2 or 20 mg/kg whole glucan particles showed 100% survival. Four times weekly oral prophylactic dosing at 2 mg/kg was not as effective as daily dosing, as a 20 mg/kg whole glucan particles dose was required to achieve significant protection (FIG. 5B).

The studies described above show that β-glucan is effective against anthrax when administered before exposure. In FIG. 6 the effect of oral whole glucan particles treatment administered after a lethal anthrax challenge on mouse survival is shown. Daily oral therapeutic dosing of whole glucan particles (>1.5 mg/kg) also significantly increased the number of anthrax survivors. Therapeutic dosing was begun one hour after infection. In these experiments, only 3 out of 10 control animals survived the anthrax infection (30% survival). In comparison, at the 1.5 mg/kg oral whole glucan particles therapeutic dose level, 80% of the treated mice survived, and at the 13.3 mg/kg oral whole glucan particles therapeutic dose level, 90% of the treated mice survived. Thus, oral whole glucan particles is effective in reducing mortality from anthrax infection even when given after exposure, in addition to its effectiveness when administered prophylactically. This is significant in that it demonstrates that β-glucan can be helpful in responding to anthrax exposure for unwarned civilians which have already been exposed, which is a likely scenario in a terrorist attack.

Additionally, the administration of β-glucan is more effective than the direct administration of cytokines such as IL-1, which are often used independently as immunomodulators, for several reasons. First, β-glucan has effects outside of its effect on cytokines, such as its ability to directly prime immune cells for activity against opsonized infectious particles. β-glucan also stimulates the endogenous release of various cellular mediators in balanced proportions, providing a stronger immune response due to the synergy of the various immune mediators induced. Finally, cytokines—being made primarily by recombinant engineering techniques—are difficult and expensive to purify, and exhibit considerable toxicity and adverse side-effects.

Furthermore, glucan polymers with immunomodulating properties all share a common β(1-3) linked linear glucose backbone. Many species, such as lentinan and scleroglucan, also contain periodic branching off the C-6 carbon atom of glucose units in their backbone. Table 1 lists a number of glucans with immunomodulatory properties and their general linkage structure as reported.

TABLE 1

| Glucans with Immunologic Activity | | |
|---|---|---|
| Glucan | Source | Linkages |
| Curdlan | *Alcaligenes faecalis* | β(1-3) |
| Soluble | *Saccharomyces* | β(1-3) |
| Phosphorylated Glucan | *Cerevisiae Coriolus* versicolor | |
| Aminated Glucan | fungi, bacteria, lichens | β(1-3) |
| Alkali-Insoluble | *Saccharomyces cerevisiae* | β(1-3)/β(1-6) |
| Yeast Glucan Lentinan | *Lentinus edodes* | β(1-3)/β(1-6) |
| Scleroglucan | *Sclerotium glucanicum* | β(1-3)/β(1-6) |
| | *Sclerotium rolfsii* | β(1-3)/β(1-6) |
| Schizophyllan | *Schizophyllan commune* | β(1-3)/β(1-6) |

Regardless of the source (e.g., organism) of the material, all the branched glucans listed in Table 1 contain at least a single glucose unit at the branch linked through a β(1-6) linkage to the backbone chain.

The anti-infective mechanism of action of β(1,3)-glucan operates primarily through the stimulation of monocytes, macrophages, neutrophils, and NK cells. Many of these cells are suppressed by toxins released by infectious particles, such as the toxins released by anthrax. Thus, β(1,3)-glucan helps directly counter the adverse effects of infection. The details of the mechanism of action of β(1,3)-glucan are described below.

Figure 8:
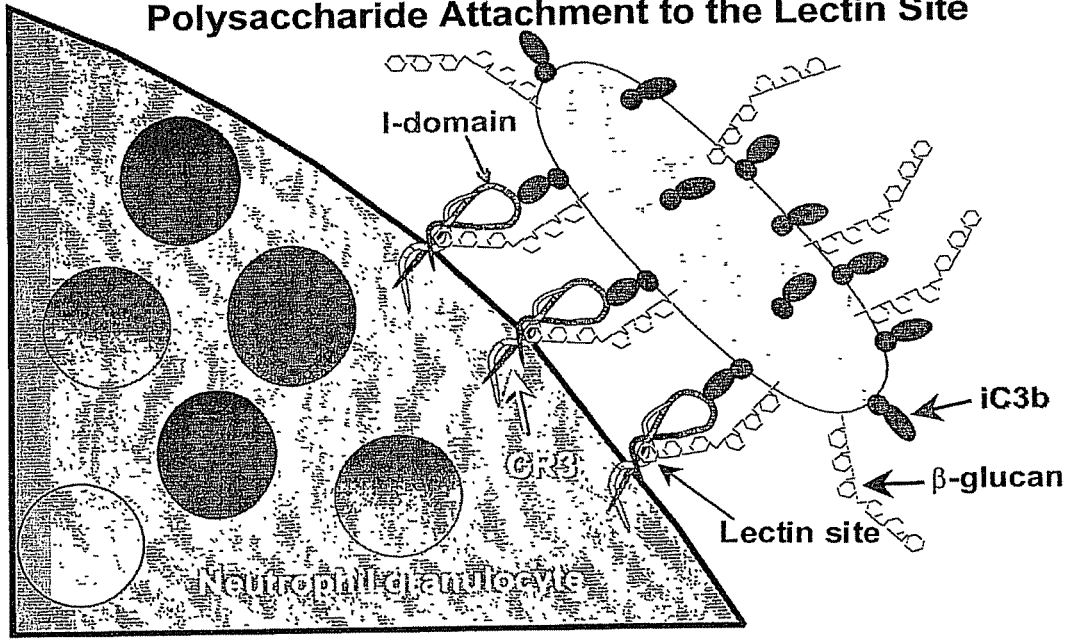
FIG. 8 is a drawing showing that activation of CR3 by C3-opsonized yeast requires both iC3b ligation and β-glucan attachment to the lectin site.

The CR3 receptor plays a very important role in the immunomodulating activity of β-glucan. The role of CR3 in mediating the response to β-glucan was shown by research into the mechanisms of neutrophil phagocytosis of iC3b-opsonized yeast. When complement C3b has attached itself to a surface, it may be clipped by a serum protein to produce a smaller fragment, iC3b. While iC3b has been "inactivated" and cannot function to form a membrane attack complex, it remains attached to the surface where it serves to attract neutrophils and macrophages which can phagocytose or otherwise destroy the marked ("opsonized") cell. On the surface of neutrophils and macrophages are type 3 complement receptors (CR3) that bind to iC3b. The process by which yeast is eliminated by the immune system is illustrated in FIG. 8.

Figure 9:
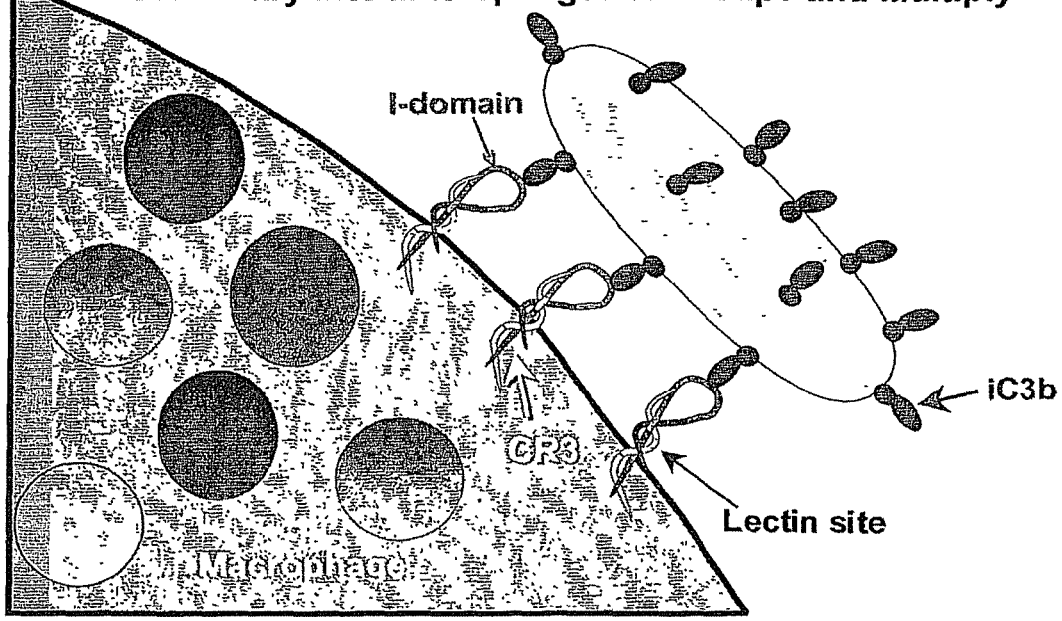
FIG. 9 is a drawing showing that bacteria lacking β-glucans do not trigger phagocytosis or degranulation via CR3.
Figure 10:
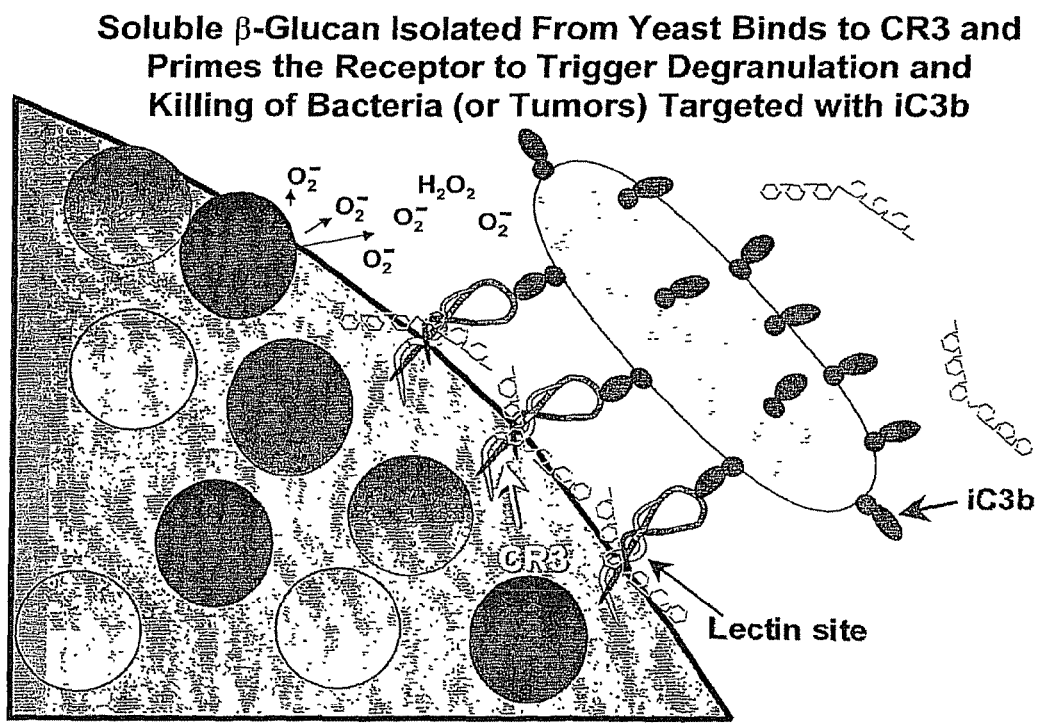
FIG. 10 is a drawing showing that soluble β-glucan binds to CR3 and primes the receptor to trigger degranulation and destruction of bacteria or tumor cells targeted with iC3b.

Stimulation of CR3-dependent phagocytosis or degranulation requires the simultaneous ligation of two distinct sites within CR3; one specific for iC3b and a second site specific for yeast cell wall β-glucan. As illustrated in FIG. 9, because they lack cell-surface CR3-binding β-glucan, bacteria opsonized with iC3b are bound to neutrophils via CR3 but do not effectively stimulate phagocytosis or degranulation. However, as illustrated in FIG. 10, addition of β-glucans can bind to the lectin site of CR3 to activate immune cells bearing the receptor to trigger degranulation and/or phagocytosis of the foreign material. Soluble zymosan-derived polysaccharides rich in mannans and β-glucans have been shown to bind to CR3 with high affinity, inducing a primed receptor state.

Figure 11:
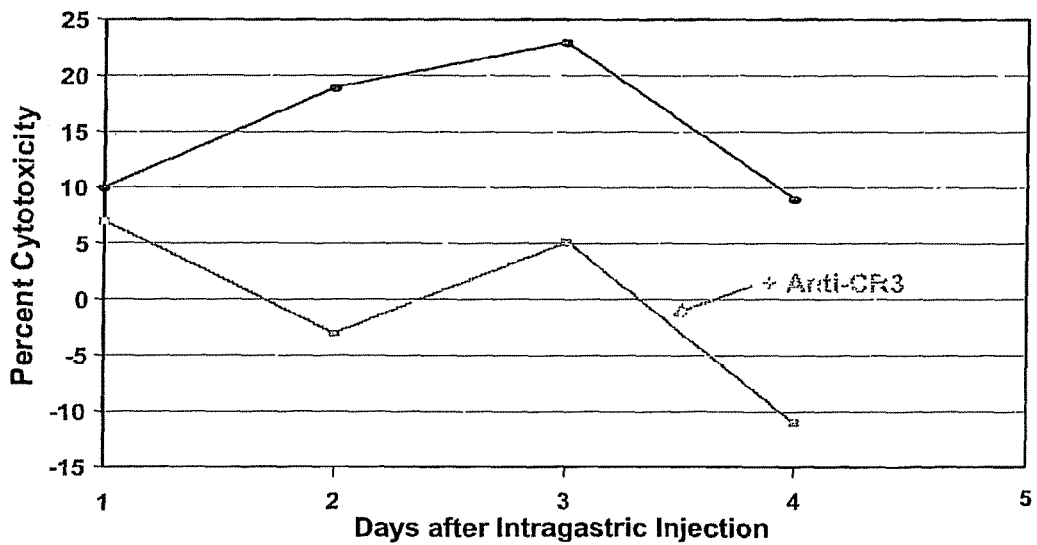
FIG. 11 is a graph showing the kinetics of splenic macrophage CR3 priming following intragastric injection of β-glucan.

FIG. 11 confirms the role of CR3 in the immunomodulation provided by βglucan. This figure shows that oral barley glucan (100 mg/Kg) induces enhanced ex vivo splenic macrophage cytotoxicity against a tumor target coated with iC3b. Co-injection of anti-CR3 mAb with oral glucan abrogates this toxicity. In specific, this figure shows the important effect of CR3 in the stimulation of the macrophage cytotoxic response by βglucan. As noted earlier, macrophages are often suppressed by harmful pathogens such as anthrax, so their activation can serve to directly counter this effect.

Figure 12:
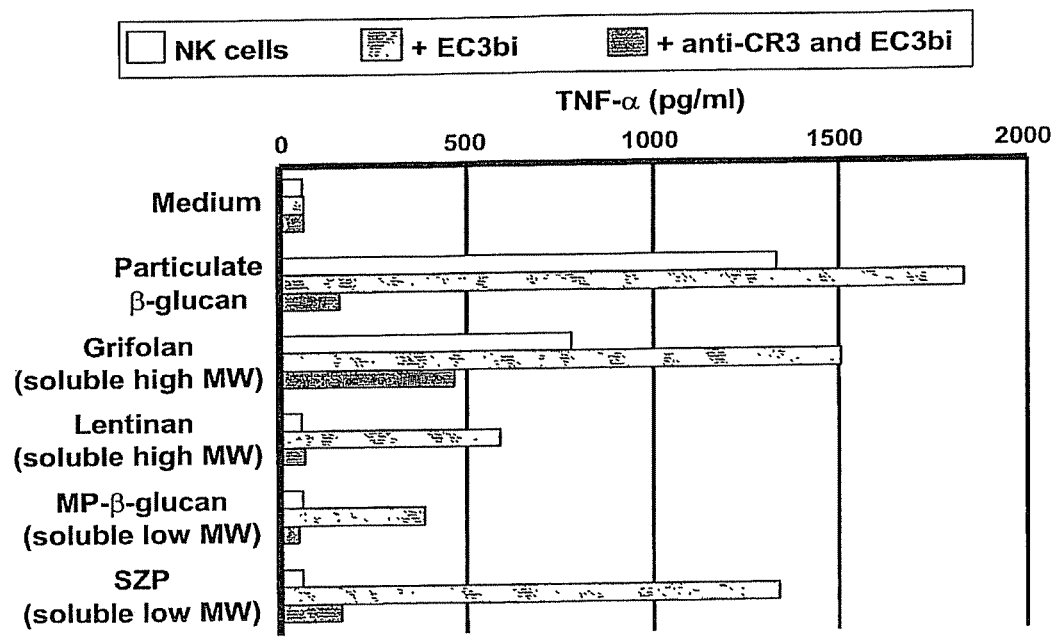
FIG. 12 is a graph showing β-glucan and CR3-dependent stimulation of NK cell secretion of TNF-α.

NK cells are another important component of the innate immune response to an infection. The function of NK cells in mediating host defense includes both direct cytotoxicity of pathogens and the secretion of cytokines such as TNF-α and IFN-γ that can potentially regulate immune responses and recruit tumoricidal macrophages. Although direct cytotoxicity of pathogens by NK cells has been shown to be mediated by the activation of CR3, additional studies have shown that this same CR3 activation event might also trigger cytokine secretion. Experiments were conducted to confirm this point, the results of which are shown in FIG. 12. Binding of small β-glucans to CR3 resulted in receptor priming for subsequent cytokine release triggered by ligation to an iC3b-opsonized target cell. The EC3bi targets did not trigger NK cell cytokine release in the absence of such polysaccharide priming, as shown in the medium control. After polysaccharide priming of CR3, ligation to an iC3b-target cell resulted in secretion of TNF-α, (as well as IFN-γ, IFN-α, and IL-6, not shown). Addition of 5 mg/ml of an anti-CD11b mAb (OKM1) blocked the secretion of all four cytokines from NK cells. Anti-CR3 blocks both β-glucan binding to CR3, as well as the binding of primed CR3 to iC3b on the EC3bi target cells.

The results shown in FIG. 12 show that NK cell secretion of cytokines occurred in parallel to CR3 activation for cytotoxicity. Particulate β-glucan, that triggers a vigorous CR3-dependent neutrophil superoxide burst, likewise triggered NK cell CR3-dependent release of cytokines. Cytokine secretion did not occur with the initial CR3 priming step that occurs with the binding of small soluble β-glucans to CR3, and occurred only secondarily with the CR3 activation step triggered by cross-linking of the β-glucan primed CR3 to an iC3b-opsonized target cell. Incubation of NK cells with EC3bi in medium alone, that does not stimulate NK cell lysis of the EC3bi, also did not trigger cytokine secretion. However, when EC3bi was added after priming of NK cell CR3 with soluble (or particulate) β-glucan, then the secretion of TNF-α, IFN-α, IFN-γ, and IL-6 was detected by ELISA. Such cytokine release was CR3-dependent because it was blocked when an anti-CD121b mAb was added at the same time as the target EC3bi.

In general, the compositions of the present invention can be administered to an individual prior to or after suspected exposure to a pathogen to increase the individual's capacity to resist infection. An individual skilled in the medical arts will be able to determine the length of time during with the composition is administered and the dosage, depending on the physical condition of the patient and the suspected pathogen. The composition may also be used on a routine basis as a preventative treatment to heighten the ability to resist infection of individuals working in situations with a higher than usual risk of exposure to harmful pathogens, such as health workers or soldiers operating in an active biological warfare environment.

The invention is further illustrated by the following Examples.

EXAMPLES

Example 1

Beta-Glucan Stimulation of NK Cell Cytokine Release

Human NK cells were cultured with either particulate yeast β-glucan or soluble CR3-binding polysaccharides for 18 hours at 37° C. Culture supernatants were then analyzed for TNF-α by ELISA. Particulate yeast β-glucan (2 μg/ml) and grifolan (≥500 kDa soluble β-glucan from *Grifola frondosa*, 2 μg/ml) are able to bind and crosslink the lectin sites of surface CR3 molecules, causing cellular activation and the secretion of both TNF-α and IL-6 (not shown). By contrast, the small (20 kDa) soluble yeast β-glucan (MP β-glucan; 2.0 μg/ml) and SZP (soluble zymosan polysaccharide preparation containing β-oligomannan and/or β-glucan; 2.0 μg/ml) bind only to individual CR3 molecules and do not trigger cytokine release in the absence of target cells. Binding of small β-glucans to CR3 resulted in receptor priming for subsequent cytokine release triggered by ligation to an iC3b-opsonized target cell (sheep erythrocytes opsonized with iC3b–"+EC3b"). The EC3bi targets did not trigger NK cell cytokine release in the absence of such polysaccharide priming, as shown in the medium control. After polysaccharide priming of CR3, ligation to an iC3b-target cell resulted in secretion of TNF-α, IFN-γ, IFN-α, and IL-6. Addition of 5 mg/ml of an anti-CD11b mAb (OKM1) blocked the secretion of all four cytokines from NK cells. Anti-CR3 blocks both β-glucan binding to CR3, as well as the binding of primed CR3 to iC3b on the EC3bi target cells.

Example 2

Beta-Glucan Treatment of Infection

A sepsis model was developed in mice to characterize the efficacy of PGG glucan in protecting an immunologically intact host against serious infections. The model used intraperitoneal challenge of mice with an 0.1 ml suspension of *E. coli* strain TVDL-rat (approximately 10 CFU/ml) 24 hours following intravenous administration of PGG by a single bolus injection using transthoracic cardiac puncture. Mice were returned to their cages and maintained on food and water, ad libitum. A control group of 10 mice were injected with 0.1 ml sterile saline at the time of the PGG administration. Mortality rates for the treatment groups and saline control group were recorded at 48 hours after challenge. The survival rate of mice given saline was 20%. However, the survival rates of mice given PGG at doses of 0.01, 0.1, 1, and 5 mg/mouse were 90%, 75%, 70% and 70% respectively. The results demonstrated that PGG significantly reduced mortality, as compared to the saline control group (p<0.05) at doses as low as 0.01 mg/mouse (0.5 mg/kg body weight).

Example 3

Anthrax Animal Model

*Bacillus anthracia* Vollum 1B, a virulent, encapsulated, toxin-producing strain (obtained from USAMRIID, Ft. Detrick, Md., USA) was propagated on blood agar plates and suspended in phosphate buffered saline (PBS), and animals challenged in a level 3-biocontainment facilities at DRES, Canada. The cell suspension was heat shocked at 80° C. for 11 min in PBS to kill vegetative cells and aliquots stored at −80° C. The frozen spore stock was diluted and used in the protection studies. Animals were maintained at a maximum of 5 mice/cage under standard laboratory condition, and water and chow were given ad libitum. Injections were performed inside Biosafety Fumehoods, on secured animals.

The anthrax model used was a well-known mouse (Balb/c) model previously described by Welkos et al. (Infect. Immun. 51:795-800, 1986). Female Balb/c mice (6 weeks old, 14 to 16 g) were purchased from Charles River. Handling of animals was performed inside BL-3 Fume hoods, on secured animals. All protocols used in these experiments were approved by the DRES Institutional Animal Care Committee (IACC) under protocol BK 01-01 and animals were cared for according to the Canadian council on Animal Care, Guide to the Care and Use of Experimental Animals, Vol. 1, 2nd edition. Five different groups of mice (10 animals/dose) were inoculated subcutaneously in the flank with approximately 1, 5, 10, $10^2$ spores from a frozen anthrax spore stock in 0.1 ml vehicle (using a 1 ml syringe, 22 gauge needle). Confirmation of the infection doses was achieved by seeding 0.1 ml of the suspension used for infection on blood agar plates. Reading of the Colony Forming Units (CFUs) was performed after a 24 h incubation period.

Example 4

Survival Rate of Anthrax-Infected Animals Treated with Systemic PGG & Whole Glucan Particles Groups of 10 animals were injected (on day −2) subcutaneously in the flank (using a 1 ml syringe, 22 gauge needle) with 50 μg/mouse of Betafectin (2.5 mg/Kg), or 200 μg/mouse of whole glucan particles (10 mg/Kg). On day 0, animals were injected subcutaneously with 214.9±97.1 anthrax spores/mouse. Control groups, which did not receive Betafectin or whole glucan particles, were included in each of the series. Confirmation of the infectiousness of the dose was made by seeding 0.1 ml of the suspension used for infection on blood agar plate. Animals were observed once a day during the first 2 days post-infection, and twice a day during the following days, until the end of the study. Mice were observed daily for 10 to 11 days (or until death) and animals found moribund were humanely sacrificed. The survival time was recorded and the $LD_{50}$ and $LD_{70}$ calculated. At day 10 or 11 post-infection all survivors were sacrificed.

Stocks of anthrax spores were titered to determine the $LD_{50}$ and the $LD_{70}$; for the anthrax model, the $LD_{50}$ was established at 227 spores/mouse and the $LD_{70}$ at 313 spores/mouse. The mean infective dose in these studies used was 214.9±97.1 spores/mouse. All experiments were performed twice. Results were presented as two independent series of data and pooled data from two experiments. Statistical analysis was performed on the two independent series of data and on the pooled data from the two experiments.

The results shown in FIG. 1 clearly demonstrate that a single dose of Betafectin (2.5 mg/Kg), or 200 μg/mouse of whole glucan particles (10 mg/Kg) significantly increased survival time. The mean survival time for the control groups infected with anthrax was 8.4/8.5 days. The mean survival time significantly increased for the groups treated with Betafectin (10.2 ($p=0.044$)/11.5 ($p=0.00029$) days) and with whole glucan particles (10.0 ($p=0.064$)/11.5 ($p=0.00029$) days). Analysis of data pooled from experiments 1 and 2 showed a statistical significant increase in the survival of mice treated with Betafectin (10.86 days) or whole glucan particles (10.80 days) when compared to control (8.45 days, $p=0.00021$ and 0.00038, respectively).

The results shown in FIG. 2 clearly demonstrate that a single dose of Betafectin (2.5 mg/Kg), or 200 μg/mouse of whole glucan particles (10 mg/Kg) significantly increased the number of survivors. In these experiments only 7 out of 22 control animals survived the observation period. In comparison, 19 of the 22 Betafectin-treated mice (86.36%; $p=0.00005$) and 18 of the 22 whole glucan particles treated mice (81.82%; $p=0.00024$) survived over the same period of time.

Example 5

Bacterial Load of Anthrax-Infected Animals Treated with Systemic PGG & Whole Glucan Particles To determine the bacterial load of anthrax-infected animals after treatment with systemic PGG and whole glucan particles, animals were infected and treated as described in Example 3. At the time of death, or at day 10 or 11 post-infection, major organs (liver, spleen, and lungs) and lymph nodes draining the infection site were harvested, weighed and homogenised in 20 ml of PBS for bacterial count. The homogenate was diluted 1/10, 1/100, 1/1000 and 1/10000 and 0.1 ml of medium and seeded on a solid culture medium (blood agar petri dishes) to evaluate the number of CFU/organ. The petri dishes were incubated at 37° C. for 24 h before counting the colonies. Each experiment was repeated once and the p values were determined using a student's T-test.

The results shown in FIGS. 3 and 4 demonstrate that a single dose of Betafectin (2.5 mg/Kg), or 200 μg/mouse of whole glucan particles (10 mg/Kg) significantly decreased bacterial load in the lung, and increased the numbers of bacteria-free mice at the end of the observation period. In these experiments, control animals displayed a bacterial load of $1.77\times10^6/3.96\times10^5$ CFU/g lung in the survivors at the end of the observation period. In comparison, the Betafectin-treated surviving animals had significantly reduced bacterial loads of $2.6\times10^5$ CFU/g lung ($p<0.05$) and the whole glucan particles-treated surviving animals had significantly reduced levels of $5.5 \times 10^5$ CFU/g lung (p<0.05). Overall, 40.9% of the control animals at the end of the observation period were bacteria-free in comparison to 86.4% of the Betafectin treated animals (p=0.0436) and 90.9% of the whole glucan particles treated animals (p=0.0194).

Example 6

Oral Prophylactic Treatment of Anthrax-Infected Mice with PGG & Whole Glucan Particles The oral prophylactic anthrax-protective effects of whole glucan particles were tested by administering a whole glucan particles suspension (40 or 400 µg/mouse) in water by gavage (daily days −7 to 0, or four times a week days −7, −4.5, −2, 0). To comply with worker safety requirements prohibiting the handling of anthrax-infected animals, the therapeutic oral protective effects of whole glucan particles were tested by administering whole glucan particles as a 0.3% w/v carboxymethylcellulose (CMC-P325G, PL Thomas) suspension in the thinking water (daily days 0 to +10) at whole glucan particles concentrations calculated to deliver daily doses of 0, 40 or 400 µg per mouse/day based on the estimated drinking water consumption of 6.5 ml water/mouse/day. Actual dosing was determined by daily measurement of water consumption, factoring the number of live animals per cage each day, and was calculated to be 0, 22.6±3.5 and 200.3±36.4 µg per mouse/day. Control groups received either vehicle gavage or carboxymethylcellulose in their drinking water only. On day 0, one hour after the oral dosing, animals were infected s.c. with an $LD_{60}$ dose anthrax spores. Animals were observed daily until the end of the study (day 10) and survival time recorded. Percent survival was calculated from the ratio of surviving animals each day to the total number of infected animals in each group (n=10). Each oral dosing experiment was carried out once. P values were determined using a Fischer exact test.

Figure 5A:
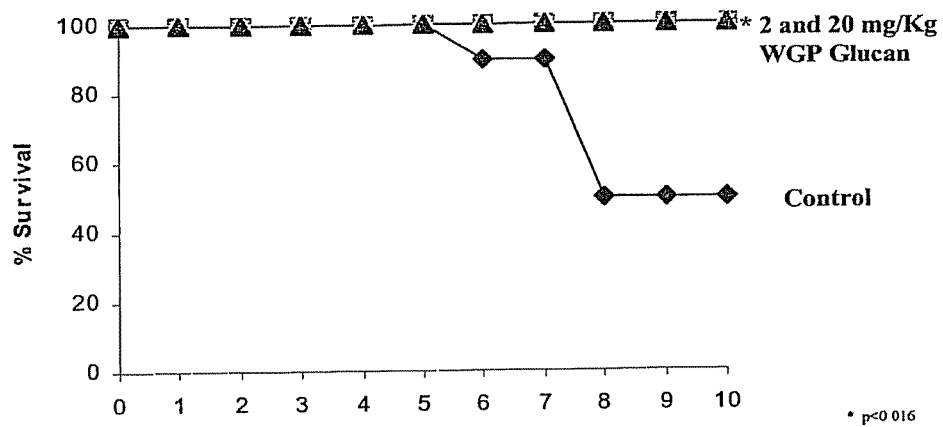
FIG. 5A is a graph of the effect of prophylactic oral whole glucan particles treatment regimen on survival to a lethal anthrax challenge.
Figure 5B:
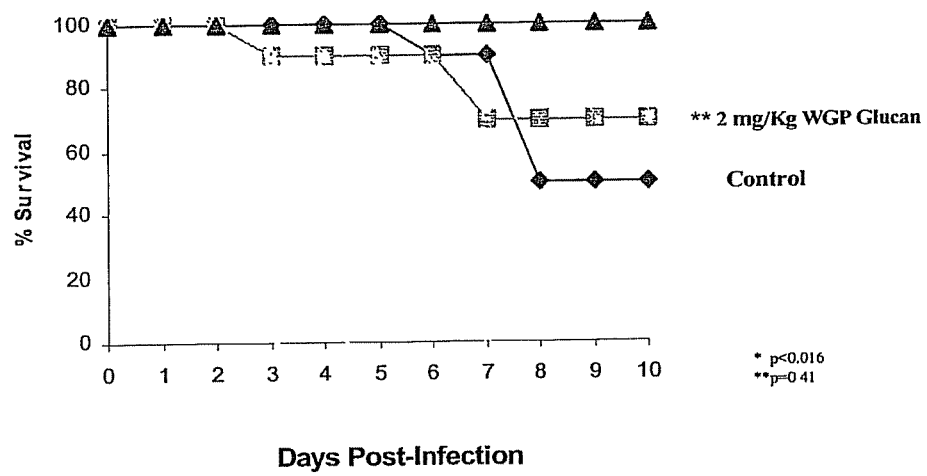
FIG. 5B is a graph of the effect of prophylactic oral whole glucan particles treatment regimen on survival to a lethal anthrax challenge.

The survival results shown in FIG. 5A demonstrate that daily oral prophylactic dosing of whole glucan particles (>2 mg/kg) also significantly increased the number of anthrax survivors. In these experiments, 5 out of 10 control animals survived the anthrax infection (50% survival). In comparison, animals treated prophylactically with daily oral doses of 2 or 20 mg/kg whole glucan particles showed 100% survival (p=0.016). In contrast, FIG. 5B shows that four times weekly oral prophylactic dosing at 2 mg/kg was not as effective as daily dosing (p=0.41), as a 20 mg/kg whole glucan particles dose was required to achieve significant protection (p=0.016).

Figure 6:
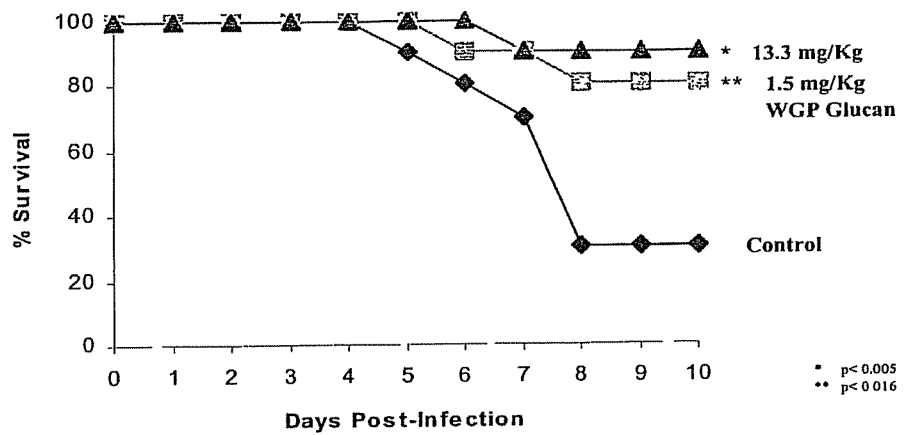
FIG. 6 is a graph of the effect of therapeutic oral whole glucan particles treatment regimen on survival to a lethal anthrax challenge.

Daily oral therapeutic dosing of whole glucan particles (>1.5 mg/kg) also significantly increased the number of anthrax survivors (FIG. 6). In these experiments 3 out of 10 control animals survived the anthrax infection (30% survival). In comparison, at the 1.5 mg/kg whole glucan particles oral therapeutic dose level, 80% of the treated mice survived (p=0.038), and at the 13.3 mg/kg whole glucan particles oral therapeutic dose level, 90% of the treated mice survived (p=0.01).

While the embodiments and applications of this invention have been shown and described in detail, it will be apparent to those skilled in the art that many more modifications than mentioned above are possible without departing from the inventive concepts described herein. The scope of the present invention is thus limited only by the terms of the appended claims.

What is claimed is:

1. A method consisting essentially of administering to a human in need of protection against infection by *Bacillus anthracis* an effective amount of underivatized, particulate β(1,3)-Glucan, wherein the human is a soldier or a health worker.

2. The method of claim 1, further comprising poly-(1,6)-β-D-glucopyranosyl-(1,3)-β-D-glucopyranose (PGG) glucan.

3. The method claim 1, wherein said β(1,3)-Glucan comprises whole glucan particles.

4. The method of claim 1, wherein said β(1,3)-Glucan comprises a combination of poly-(1,6)-β-D-glucopyranosyl-(1,3)-β-D-glucopyranose (PGG) glucan and whole glucan particles.

5. The method of claim 2, wherein about 0.1-100 mg/Kg of poly-(1,6)-β-D-glucopyranosyl-(1,3)-β-D-glucopyranose (PGG) glucan is administered daily.

6. The method of claim 3, wherein greater than 0.01 mg/Kg of whole glucan particles is administered daily.

7. The method of claim 4, wherein a combination of about 0.1-100 mg/Kg of poly-(1,6)-β-D-glucopyranosyl-(1,3)-β-D-glucopyranose (PGG) and about 0.1-500 mg/Kg of whole glucan particles is administered daily.

8. The method of claim 2, wherein about 1-10 mg/Kg of poly-(1,6)-β-D-glucopyranosyl-(1,3)-β-D-glucopyranose (PGG) is administered daily.

9. The method claim 3, wherein about 10 mg/Kg of whole glucan particles is administered daily.

10. The method of claim 4, wherein a combination of about 1-10 mg/Kg of poly-(1,6)-β-D-glucopyranosyl-(1,3)-β-D-glucopyranose (PGG) and about 2-20 mg/Kg of whole glucan particles is administered daily.

11. The method of claim 1, wherein the β(1,3)-Glucan is administered orally, topically, subcutaneously, intramuscularly, transdermally, intradermally, intravenously, or through the gastrointestinal tract.

12. The method of claim 1, wherein the β(1,3)-Glucan is administered orally.

* * * * *